（12）United States Patent
Iannotti et al.

(10) Patent No.: US 9,216,046 B2
(45) Date of Patent: Dec. 22, 2015

(54) METHODS AND DEVICES FOR BONE PREPARATION

(76) Inventors: Joseph P. Iannotti, Strongsville, OH (US); Peter M. Bonutti, Effingham, IL (US)

(*) Notice: Subject to any disclaimer, the term of this patent is extended or adjusted under 35 U.S.C. 154(b) by 814 days.

(21) Appl. No.: 13/443,555

(22) Filed: Apr. 10, 2012

(65) Prior Publication Data

US 2012/0259312 A1    Oct. 11, 2012

Related U.S. Application Data

(60) Provisional application No. 61/473,805, filed on Apr. 10, 2011.

(51) Int. Cl.
*A61B 17/88* (2006.01)
*A61F 2/30* (2006.01)

(52) U.S. Cl.
CPC ......... *A61B 17/8802* (2013.01); *A61B 17/8816* (2013.01); *A61F 2002/30677* (2013.01)

(58) Field of Classification Search
CPC ............... A61B 17/88; A61B 17/8802; A61B 17/8805; A61B 17/8808; A61B 17/8811; A61B 17/8816; A61F 2002/30677
See application file for complete search history.

(56) References Cited

U.S. PATENT DOCUMENTS

| | | | |
|---|---|---|---|
| 4,274,163 A * | 6/1981 | Malcom et al. | 606/94 |
| 4,441,492 A * | 4/1984 | Rydell et al. | 606/67 |
| 4,462,394 A | 7/1984 | Jacobs | |
| 4,653,489 A * | 3/1987 | Tronzo | 606/65 |
| 5,037,437 A | 8/1991 | Matsen, III | |
| 5,114,240 A * | 5/1992 | Kindt-Larsen et al. | 366/129 |
| 5,116,377 A * | 5/1992 | Skripitz et al. | 623/23.19 |
| 5,192,282 A * | 3/1993 | Draenert | 606/65 |
| 5,312,408 A * | 5/1994 | Brown | 606/80 |
| 5,344,458 A * | 9/1994 | Bonutti | 623/20.32 |
| 5,520,667 A | 5/1996 | Roche | |
| 5,554,111 A * | 9/1996 | Morrey et al. | 604/26 |
| 5,558,646 A | 9/1996 | Roche | |
| 5,681,289 A * | 10/1997 | Wilcox et al. | 604/175 |
| 5,704,909 A | 1/1998 | Morrey et al. | |
| 5,800,439 A | 9/1998 | Clyburn | |

(Continued)

OTHER PUBLICATIONS

International Search Report and Written Opinion, mailing date May 31, 2012, pp. 1-14.

*Primary Examiner* — Christian Sevilla
*Assistant Examiner* — Eric S Gibson
(74) *Attorney, Agent, or Firm* — Tummino, Sundheim, Covell & Tummino LLP

(57) ABSTRACT

A manifold has at least one manifold aperture extending therethrough and selectively placed in fluid communication with a fluid source. An insertion structure has at least one interior cavity at least partially defined by a structure shell and is selectively placed in fluid communication with a corresponding manifold aperture. The insertion structure is configured for selective placement in a penetrating relationship with a patient tissue below a surface of the patient tissue. At least one shell perforation extends through the structure shell and places the interior cavity in fluid communication with a surrounding ambient space. At least one fluid path extends from the fluid source, through the manifold aperture, into the interior cavity, through at least one shell perforation, and at least one of a proximate relationship and a contacting relationship with the patient tissue beneath the outer surface thereof. A fluid is directed along the fluid path.

8 Claims, 30 Drawing Sheets

(56) References Cited

U.S. PATENT DOCUMENTS

| | | | |
|---|---|---|---|
| 5,947,893 A | 9/1999 | Agrawal et al. | |
| 6,197,032 B1* | 3/2001 | Lawes et al. | 606/91 |
| 6,214,012 B1* | 4/2001 | Karpman et al. | 606/93 |
| 6,370,418 B1 | 4/2002 | Bernoski | |
| 6,428,579 B1 | 8/2002 | Valentini | |
| 6,461,385 B1* | 10/2002 | Gayer et al. | 623/23.51 |
| 6,502,608 B1* | 1/2003 | Burchett et al. | 141/386 |
| 6,840,960 B2 | 1/2005 | Bubb | |
| 7,029,431 B2 | 4/2006 | Apple et al. | |
| 7,250,055 B1* | 7/2007 | Vanderwalle | 606/92 |
| 7,524,334 B2 | 4/2009 | Haidukewych | |
| 7,717,947 B1* | 5/2010 | Wilberg et al. | 606/304 |
| 7,749,279 B2 | 7/2010 | Twomey et al. | |
| 2002/0049448 A1* | 4/2002 | Sand et al. | 606/92 |
| 2002/0173770 A1* | 11/2002 | Flory et al. | 604/537 |
| 2002/0173796 A1* | 11/2002 | Cragg | 606/86 |
| 2004/0225292 A1* | 11/2004 | Sasso et al. | 606/73 |
| 2005/0080490 A1* | 4/2005 | Bertram, III | 623/22.28 |
| 2005/0228397 A1* | 10/2005 | Malandain et al. | 606/93 |
| 2007/0161985 A1* | 7/2007 | Demakas et al. | 606/61 |
| 2007/0233099 A1* | 10/2007 | Cragg | 606/61 |
| 2007/0233123 A1* | 10/2007 | Ahmad et al. | 606/73 |
| 2007/0299450 A1* | 12/2007 | Her et al. | 606/73 |
| 2008/0071281 A1* | 3/2008 | Wilson et al. | 606/92 |
| 2008/0086072 A1* | 4/2008 | Bonutti et al. | 604/21 |
| 2008/0208260 A1* | 8/2008 | Truckai et al. | 606/280 |
| 2008/0269761 A1* | 10/2008 | Truckai et al. | 606/94 |
| 2009/0069899 A1* | 3/2009 | Klein | 623/22.4 |
| 2009/0131947 A1* | 5/2009 | Aeschlimann et al. | 606/93 |
| 2009/0143826 A1* | 6/2009 | Birkenbach et al. | 606/301 |
| 2010/0042214 A1* | 2/2010 | Nebosky et al. | 623/16.11 |
| 2010/0174320 A1* | 7/2010 | Truckai et al. | 606/279 |
| 2010/0211120 A1* | 8/2010 | Bonutti et al. | 606/86 R |
| 2010/0241229 A1* | 9/2010 | Baehre et al. | 623/16.11 |
| 2010/0256690 A1* | 10/2010 | Appenzeller et al. | 606/305 |
| 2011/0035013 A1* | 2/2011 | Winslow et al. | 623/19.13 |
| 2011/0060373 A1* | 3/2011 | Russell et al. | 606/304 |
| 2011/0125156 A1* | 5/2011 | Sharkey et al. | 606/92 |
| 2012/0109137 A1* | 5/2012 | Iannotti et al. | 606/87 |
| 2012/0259312 A1* | 10/2012 | Iannotti et al. | 604/506 |
| 2012/0277754 A1* | 11/2012 | Lin et al. | 606/93 |
| 2013/0110115 A1* | 5/2013 | Lackman | 606/94 |
| 2013/0110120 A1* | 5/2013 | Baroud et al. | 606/102 |
| 2013/0231654 A1* | 9/2013 | Germain | 606/33 |
| 2013/0236874 A1* | 9/2013 | Iannotti et al. | 434/274 |
| 2014/0039454 A1* | 2/2014 | Sharkey | 604/506 |
| 2014/0142550 A1* | 5/2014 | Sweeney | 604/513 |
| 2014/0142584 A1* | 5/2014 | Sweeney | 606/103 |
| 2014/0257418 A1* | 9/2014 | Arthur | 606/86 R |
| 2014/0276561 A1* | 9/2014 | Arthur et al. | 604/506 |
| 2014/0276875 A1* | 9/2014 | Arthur et al. | 606/93 |
| 2014/0276876 A1* | 9/2014 | Arthur et al. | 606/93 |
| 2014/0373922 A1* | 12/2014 | Geppert et al. | 137/1 |

* cited by examiner

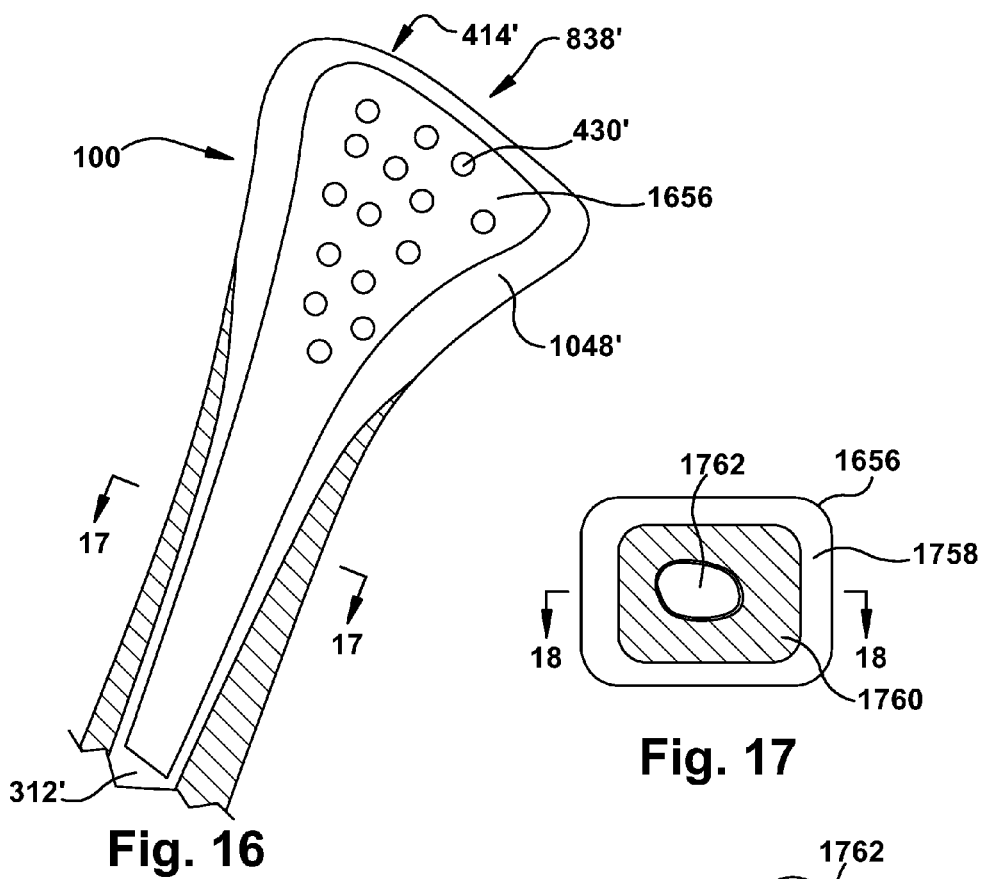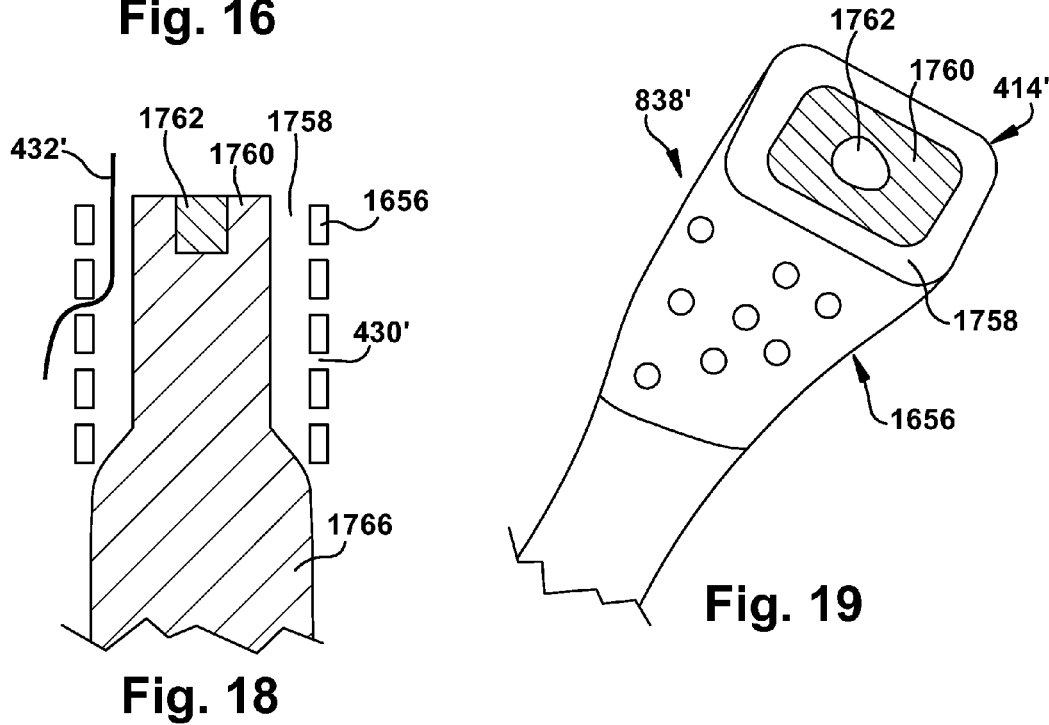
Fig. 16
Fig. 17
Fig. 18
Fig. 19

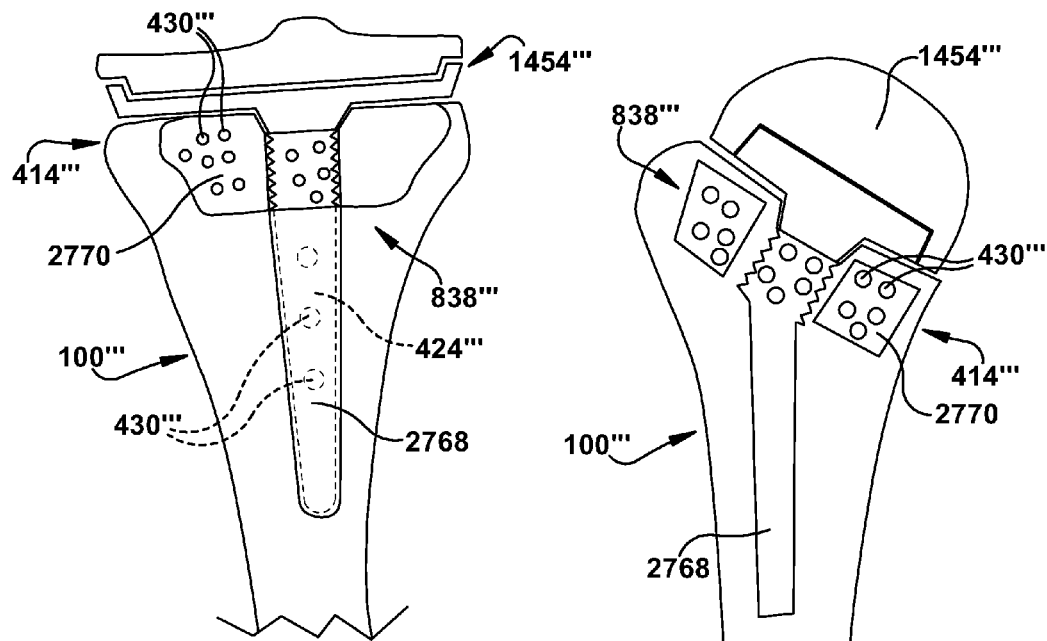
Fig. 29
Fig. 30
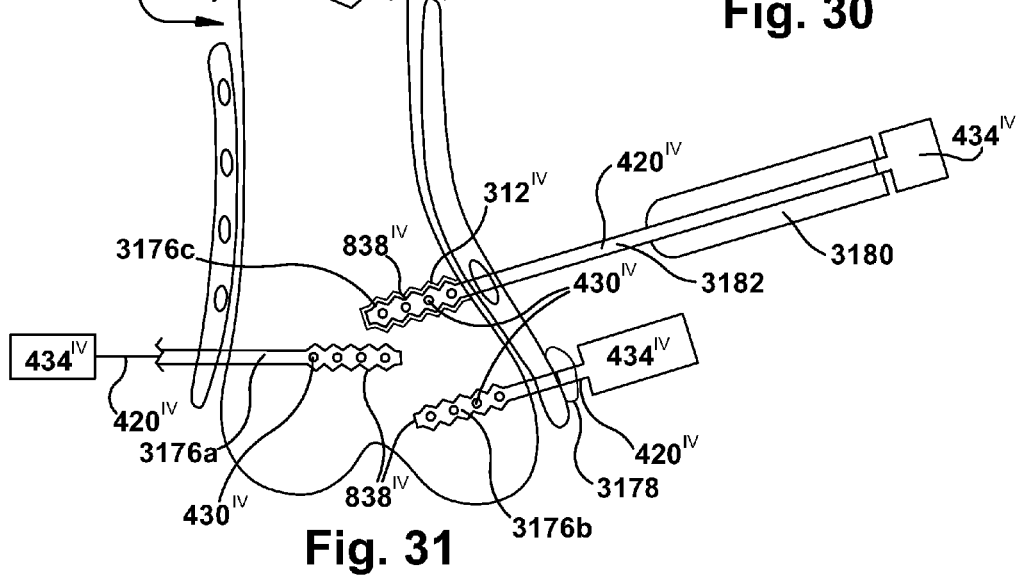
Fig. 31

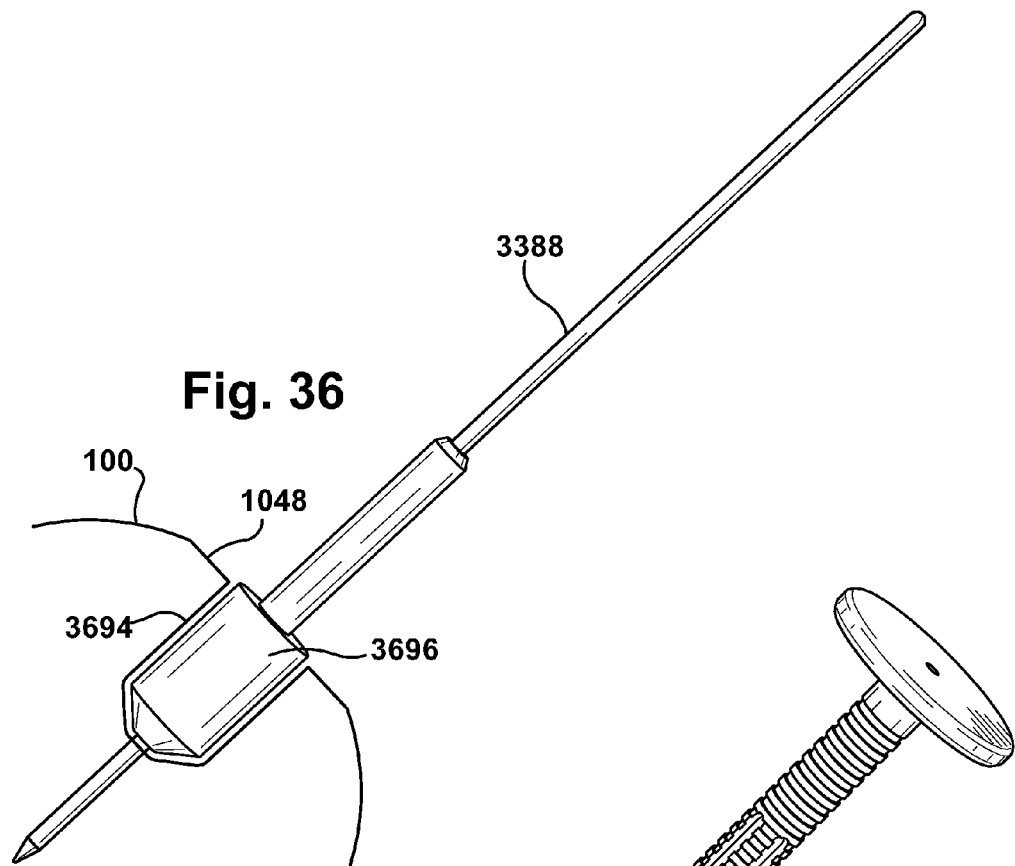
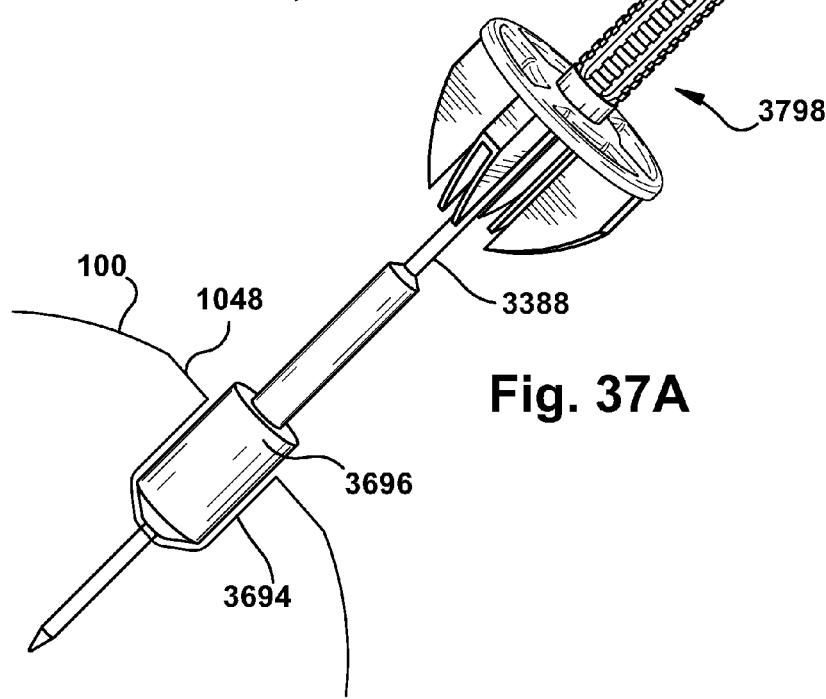

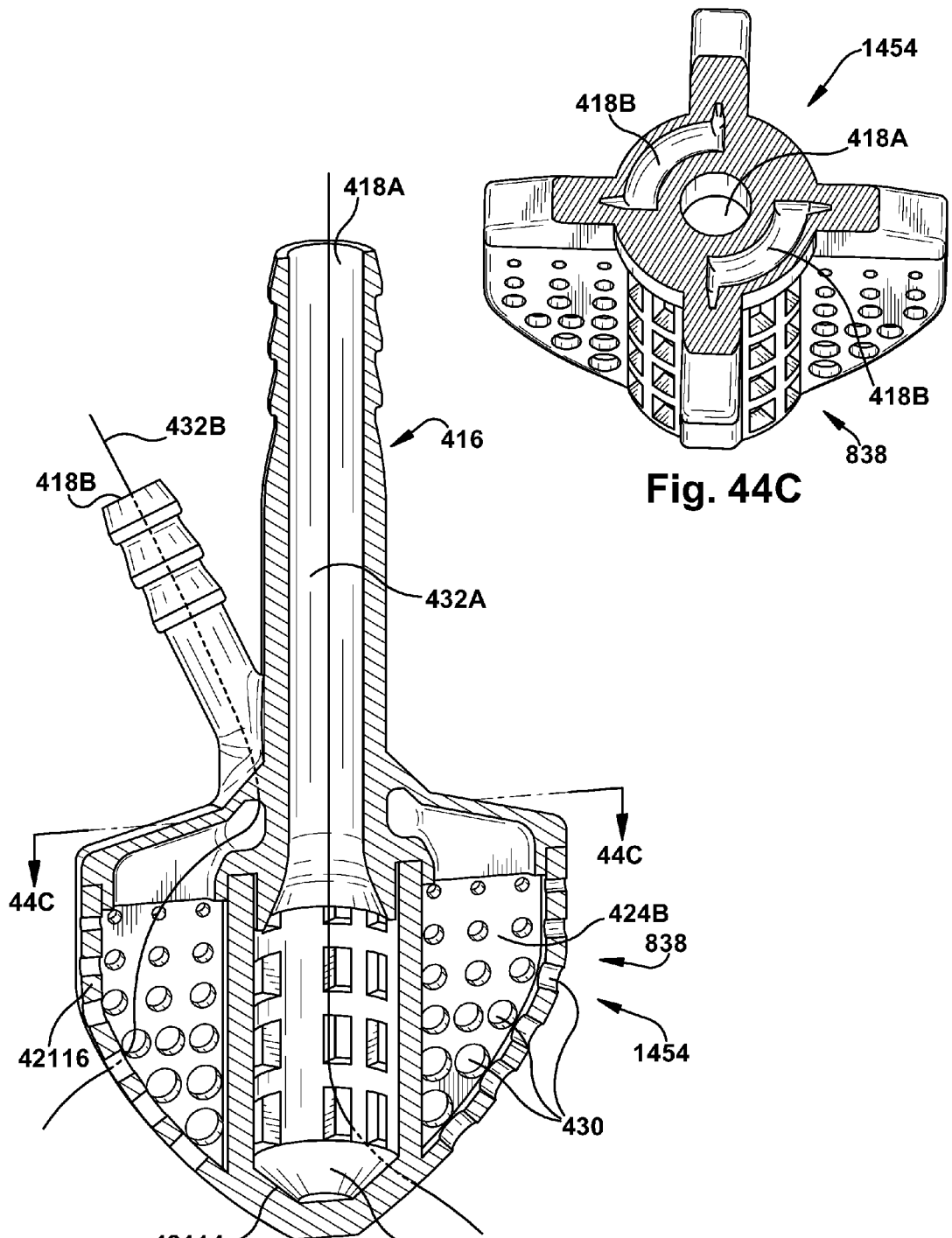

METHODS AND DEVICES FOR BONE PREPARATION

RELATED APPLICATION

This application claims priority from U.S. Provisional Application No. 61/473,805, filed Apr. 10, 2011, the subject matter of which is incorporated herein by reference in its entirety.

TECHNICAL FIELD

The present invention relates to an apparatus and method for use of a bone preparation device and, more particularly, to methods and devices for bone preparation which assist with supplying fluid to, or removing fluid from, the bone surface.

BACKGROUND OF THE INVENTION

The stability of an implant in bone may be determined by the shape of the implant, the quality of the bone, and/or the preparation of the surgical site. In many cases, the bone quality may be weakened due to aging or disease. Weakened bone—or even normal cancellous (i.e., porous) bone—may lack sufficient support for traditional implantation techniques. As one solution, the bone may be augmented with bone graft in the area around a space made for placement of the implant, which may performed by impaction grafting of cancellous autograft or allograft tissue and/or the addition of a bone graft substitute. As another approach, the implant may be fixed by adding bone cement to the cavity, potentially under pressure to assist penetration of the bone cement a distance from the space created for the implant and/or against the surrounding tissue. Traditional methods may not provide sufficient access for preparing bone or adding bone augmentation materials.

Traditional systems and techniques for bone preparation may not reach the areas in which the implant is positioned and may cause tissue bleeding between the preparation of bone and implantation of the implant. Traditional techniques may be more complex and time consuming, lack the characteristic of being employed with precision, be damaging to tissue, and/or fail to provide for proper preparation of weakened and/or cancellous bone, for example, at a site distant from the bone surrounding the implant or around the cavity in the bone created by the broach or instrument. As such, there is a need for an apparatus and method for preparing, accessing, and/or fastening to, for example, weak and/or cancellous tissue, such as an apparatus for preparing bone tissue deep into the surface of the bone including sites that surround the implant but are a distance from the bone immediately around the implant.

SUMMARY OF THE INVENTION

In an embodiment of the present invention, an apparatus for patient tissue preparation is described. A manifold has at least one manifold aperture extending therethrough. The manifold aperture is selectively placed in fluid communication with a fluid source. An insertion structure has at least one interior cavity at least partially defined by a structure shell. The interior cavity is selectively placed in fluid communication with a corresponding manifold aperture. The insertion structure is configured for selective placement in a penetrating relationship with a patient tissue below a surface of the patient tissue. At least one shell perforation extends through the structure shell and places the interior cavity in fluid communication with a surrounding ambient space. When the insertion structure is in the penetrating relationship with the patient tissue, at least one fluid path extends from the fluid source, through the manifold aperture, into the interior cavity, through at least one shell perforation, and at least one of a proximate relationship and a contacting relationship with the patient tissue beneath the outer surface thereof. A fluid is directed along the fluid path to perform a patient tissue preparation task.

In an embodiment of the present invention, a method for patient tissue preparation is described. A manifold having at least one manifold aperture extending therethrough is provided. The manifold aperture is placed in fluid communication with a fluid source. An insertion structure is provided, having at least one interior cavity at least partially defined by a structure shell. The interior cavity is placed in fluid communication with a corresponding manifold aperture. The insertion structure is selectively placed in a penetrating relationship with a patient tissue below a surface of the patient tissue. At least one shell perforation extending through the structure shell is provided. The interior cavity is placed in fluid communication with a surrounding ambient space through at least one shell perforation. When the insertion structure is in the penetrating relationship with the patient tissue, at least one fluid path is created extending from the fluid source, through the manifold aperture, into the interior cavity, through at least one shell perforation, and into at least one of a proximate relationship and a contacting relationship with the patient tissue beneath the outer surface thereof. A fluid is directed along the fluid path to perform a patient tissue preparation task.

In an embodiment of the present invention, a prosthetic implant component installation system is described. A manifold has at least one manifold aperture in a surface thereof. The manifold aperture is selectively placed in fluid communication with a fluid source. An implant structure has at least one interior cavity at least partially defined by a relatively thin-walled structure shell such that a higher percentage of the total implant structure volume is dedicated to interior cavity space than is provided by the structure shell. The interior cavity is selectively placed in fluid communication with a corresponding manifold aperture. The implant structure is configured for selective placement in a penetrating relationship with a patient tissue below a surface of the patient tissue to provide an ongoing, at least semi-permanent therapeutic function to the patient tissue. The implant structure is selectively mated with the manifold during a surgical procedure for fluid communication therewith. The manifold is removed from the mating relationship with the implant structure before the surgical procedure concludes. At least one shell perforation extends through the structure shell and places the interior cavity in fluid communication with a surrounding ambient space. When the implant structure is in the penetrating relationship with the patient tissue and the manifold is mated with the implant structure, a plurality of separate fluid paths are each defined through a chosen manifold aperture, into a corresponding chosen interior cavity, through at least one shell perforation of the chosen interior cavity, and into at least one of a proximate relationship and a contacting relationship with the patient tissue beneath the outer surface thereof. A fluid is directed along at least one fluid path to perform a patient tissue preparation task.

BRIEF DESCRIPTION OF THE DRAWINGS

For a better understanding of the invention, reference may be made to the accompanying drawings, in which:

FIG. 16 is a side view of an embodiment of the present invention;

FIG. 17 is a cross-section taken along line 17-17 in FIG. 16;

FIG. 18 is a cross-section taken along line 18-18 in FIG. 17;

FIG. 19 is a partial perspective view of the embodiment of FIG. 16;

FIG. 29 is a side view of an embodiment of the present invention in the example use environment of FIG. 26;

FIG. 30 is a side view of an embodiment of the present invention in the example use environment of FIG. 20A;

FIG. 31 is a side view of an embodiment of the present invention in an example use environment;

FIG. 36 is a side view of a tool for use with an embodiment of the present invention;

FIG. 37A is an exploded side view of a tool for use with an embodiment of the present invention;

FIG. 44B is a cross-sectional view taken along line B-B of FIG. 44A;

FIG. 44C is a cross-sectional view taken along line C-C of FIGS. 44A and 44B;

DESCRIPTION OF EMBODIMENTS

Figures 1, 2, 3:
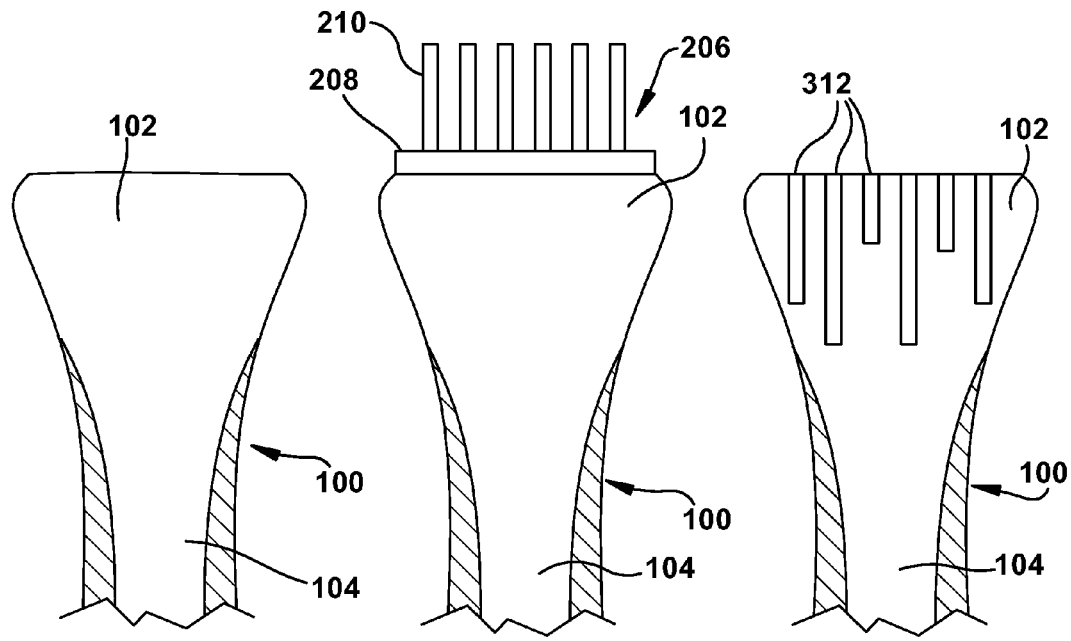
FIG. 1 is a partial side view of an example use environment for the present invention.
FIG. 2 is a partial side view of an embodiment of the present invention in the use environment of FIG. 1.
FIG. 3 is a partial side view of the embodiment of FIG. 2 in the use environment of FIG. 1.

Devices and methods of the present disclosure may be applied to any patient tissue surface, such as a cancellous bone surface, for any type of surgery, including, but not limited to, an implant for joint reconstruction, joint replacement, fracture fixation, or any other joint or spinal procedure. For example, embodiments may be used for the proximal humerus metaphysis for a shoulder arthroplasty that may obtain fixation from the metaphyseal and or diaphyseal bone. The final implant within the metaphysis may allow for the application of any articulating device for shoulder replacement. Embodiments may include placement of a spherical or semi-elliptical head or a component for reverse shoulder arthroplasty. Embodiments may be applied to any bone surface to include the distal femur or proximal tibia for total knee arthroplasty, the distal tibia or talus for ankle arthroplasty, the distal radius for fracture fixation or wrist arthroplasty, or the acetabulum for hip arthroplasty.

Embodiments may be configured for augmentation of a portion or all of the metaphysis of the bone, and optionally a majority thereof. The implant may be placed to minimize disruption of the bone in areas around the implant and/or minimize disruption of the bone in areas spaced apart from the main functional portion of the implant, which may not have been accessible from the space created for the implant (such as areas for accommodating a keel, peg, stem, or other structure of the implant). Use of bioactive materials may enhance bone structure (which may include bone matrix), allow for enhanced implant fixation, and/or be incorporated into the bone.

The methods and devices disclosed in the present disclosure may be used in conjunction with any medical procedure on the body, for example, during intervertebral disc surgery, kyphoplasty, knee surgery, hip surgery, organ transplant surgery, bariatric surgery, spinal surgery, anterior cruciate ligament ("ACL") surgery, posterior cruciate ligament ("PCL") surgery, tendon-ligament surgery, rotator cuff surgery, capsule repair surgery, fractured bone surgery, pelvic fracture surgery, avulsion fragment surgery, shoulder surgery, hernia repair surgery, and/or surgery for an intrasubstance ligament tear, annulus fibrosis, fascia lata, flexor tendons, or any other type of medical procedure.

As additional examples, applications for embodiments may include any type of prosthetic replacement devices that are implemented into possibly weak and/or cancellous bone. For example, this may include hip, knee, and shoulder replacements, internal fixation devices for fractures or fracture sequelae, suture anchors for soft tissue to bone repair, and external fixation devices. As a further example, embodiments may be used for orthopedic surgery, maxillofacial surgery, dental implants, or any other patient tissue operation.

In the attached Figures, multiple instances of similar structures in the same Figure have not all been labeled with element numbers, to avoid undue visual clutter and resulting confusion. One of ordinary skill in the art will understand that, in a Figure having at least one structure called out with an element number, similar structures can be considered to have the same element number.

FIG. 1 depicts a schematic side view of a patient tissue, shown here as a bone 100 (a long bone, in FIG. 1), which has a metaphysic region 102 including cancellous bone and a diaphysis region 104 including cortical bone and a medullary canal.

The patient tissue is shown and described herein at least as a humerus and the prosthetic implant component is shown and described herein at least as a prosthetic shoulder component, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention.

Figures 4, 5:
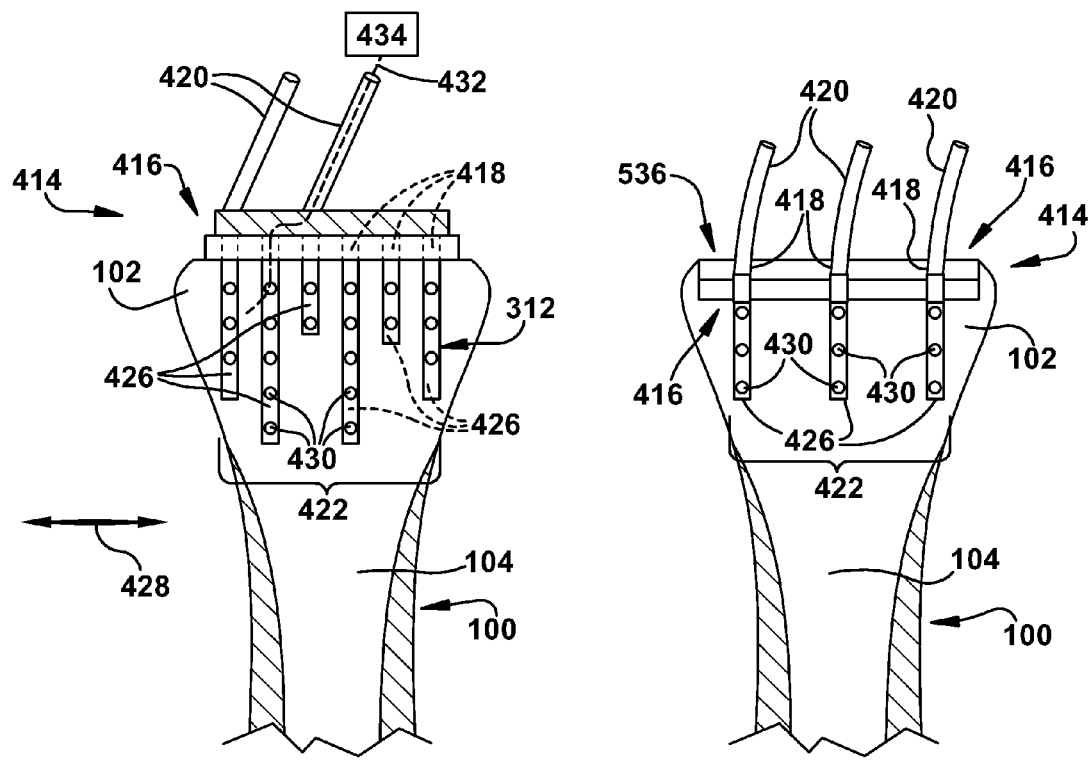
FIG. 4 is a partial side view of the embodiment of FIG. 2 in the use environment of FIG. 1.
FIG. 5 is a partial side view of the embodiment of FIG. 2 in the use environment of FIG. 1.
Figure 6:
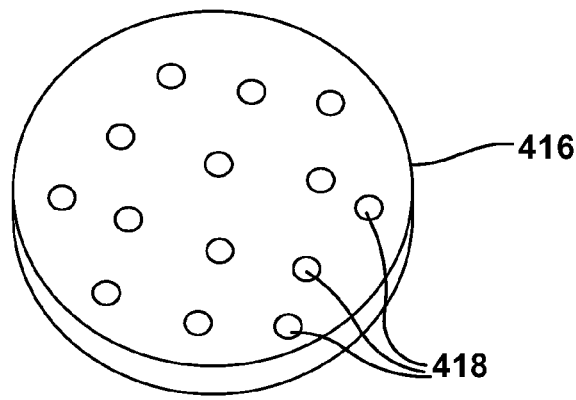
FIG. 6 is a top view of an embodiment of the present invention.

The sequence of operations depicted in FIGS. 2-4 illustrates an example of a use procedure for an embodiment of the present invention. In FIG. 2, the bone 100 is provided with a guide 206, which may be a stock component or which may instead be a patient-specific component. In the latter case, the guide 206 may be preoperatively designed and manufactured in any suitable manner. The guide 206 is configured to sit on a desired bone 100 surface; in FIG. 2, this is the topmost bone surface. The guide 206 includes a guide plate 208, which contacts the patient tissue surface, and a plurality of guide tubes 210 (permanently attached to the guide plate or removable therefrom) which function to guide an elongate tool, such as a drill or osteotome, into the underlying patient tissue at predetermined locations and/or depths.

FIG. 3 depicts the bone 100 after the guide 206 has been used to at least partially dictate the location and/or depth of a plurality of cavities 312 in the bone. The present invention is agnostic and apathetic as to the manner by which one or more cavities 312 are provided in the patient tissue, and it will be presumed herein that a naturally occurring or at least partially manmade (e.g., hand-machined during the surgical procedure) cavity is present in the patient tissue without restriction as to its origin. For example, the cavity 312 may be created, at least in part, by a structure of the present invention during operation as described herein.

In FIG. 4, a bone preparation apparatus 414 is shown mated with the bone 100. The term "mate" is used herein to indicate a relationship between two separate structures which are joined or fitted together closely because they have similar three-dimensional shapes (e.g., a positive and a negative version of the same contour, respectively). Two structures in a "mated" relationship may include at least some space therebetween, or may even have a thin interposed structure (e.g., a cushion or membrane), but should be configured to fit substantially closely together at the mated interface. The bone preparation apparatus 414 may be mated with at least a portion of the surrounding bone 100, or these structures may be spaced apart in any desired manner, and by any desired amount. Element 414 is referred to herein as a "bone preparation" apparatus, for ease of description, but could be used for any reason (preparation tasks or otherwise), and in any patient tissue(s), not just bone.

The bone preparation apparatus 414 includes a manifold 416 having at least one manifold aperture 418 extending therethrough. The manifold aperture 418 may be selectively placed in fluid communication with a fluid source (not shown), through the agency of a structure such as the fluid lines 420 shown in FIG. 4. Optionally, the fluid lines 420 may be in fluid communication with a relatively large compartment (not shown) or "tank" in the manifold, for provision of fluid to any of a number of tubes 422 which are also in fluid communication with the compartment. When this is the case, multiple fluids could be provided to the compartment, via separate fluid lines 420, for admixture therein and subsequent provision of a mixed fluid to the tubes 422. Alternately, each fluid line 420 may be directly connected to one or more tubes 422, with no reservoir located therebetween. As used herein, the term "manifold" is intended to mean any structure or other means which acts to direct fluid between a fluid source 434 and an insertion structure. Accordingly, a fluid line 420 could perform a "manifold" function for a particular embodiment of the present invention and obviate the need for a separate manifold 416 structure. One of ordinary skill in the art will realize that the fluid lines 420 and manifold 416 described herein may be either the same or separate components, and will be able to readily provide fluid lines and/or manifolds for a particular application of the present invention.

The bone preparation apparatus 414 also includes an insertion structure (here, a plurality of tubes 422) having at least one interior cavity 424 at least partially defined by a structure shell 426. The interior cavity 424 of at least one insertion structure is selectively placed in fluid communication with a corresponding manifold aperture 418. In the embodiment of FIGS. 4 and 5, the interior cavities 424 are the lumens of, and the structure shell 426 is the tubular circumference of, the plurality of tubes 422 ("insertion structures") shown. The tubes 422 may be at least semi-permanently attached to the manifold 416, the bone 100 and/or the fluid source, or the tubes may be temporary and readily removable from engagement with one or more of these other structures.

As shown in FIG. 4, the tubes 422 may be mated with the previously prepared cavities 312, extending into the patient tissue below/beneath (i.e., deeper than) an outer surface thereof. That is, the tubes 422 are configured for selective placement in a penetrating relationship with a patient tissue below (i.e., further downward on the page in the orientation of FIG. 4) the surface of the patient tissue. It is contemplated that one insertion structure will be provided for each cavity 312 in most embodiments of the present invention, and that the cavity will have been machined, formed, or otherwise suited to mating insertion of a correspondingly shaped insertion structure. Here, the tubes 422 mate closely with the cavities 312 in the patient tissue, but a more general relationship in which the tube is merely inserted into some portion of a substantially larger cavity, is also possible without harm to the present invention.

Optionally, and as shown in FIG. 4, when the tubes 422 are in the penetrating relationship with the bone 100, it is possible for some bone 100 or other patient tissue to be interposed laterally between any two tubes. Lateral arrow 428 shows the lateral direction in FIG. 4, which also extends into and out of the plane of the page.

It is contemplated that, when multiple interior cavities 424 of a bone preparation apparatus 414 are present, at least one interior cavity may have a different physical configuration property (e.g., length, width, cross-sectional shape, material of the associated insertion structure, or any other physical property) from another one of the interior cavities. As shown in FIG. 4, the plurality of tubes 422 are all depicted schematically as having similar diameters, but have very different lengths to which they extend into the bone 100. This variety of insertion depths can be provided using various-length tubes 422 and/or using same-length tubes inserted in a variable manner, to different depths.

At least one shell perforation 430 extends through the structure shell 426 and places the interior cavity 424 in fluid communication with a surrounding ambient space, such as the patient tissue into which the cavities 312 are bored, whether or not the patient tissue forming the cavities is in direct contact with the structure shell 426. In this manner, the tubes 422 serve as conduits or access means penetrating into the depth of a patient tissue. It is contemplated that, when multiple shell perforations 430 are present, at least one shell perforation may have a different physical configuration property (e.g., length, width, perimeter shape, angle of penetration through the structure shell 426, or any other physical property) from another one of the shell perforations.

When the insertion structure (here, tubes 422) is in a penetrating relationship, similar to that shown in FIG. 4, with a patient tissue, such as the bone 100, at least one fluid path 432 is created. The fluid path 432 extends from a fluid source 434 of any suitable type, optionally through a manifold aperture 418 (when present), into an interior cavity 424, through at least one shell perforation 430, and into at least one of a proximate relationship and a contacting relationship with the patient tissue at any suitable penetration or insertion depth below the surface of the patient tissue. A proximate relationship is one in which the fluid path 432 extends close to the patient tissue. A contacting relationship is one in which the fluid path 432 directly touches the patient tissue. A relationship may be both proximate and contacting in different areas at the same time, either proximate or contacting but not both, or may be proximate at one time and contacting at another time. An example of one suitable fluid path 432 is shown in dashed line in FIG. 4, but one of ordinary skill in the art will be able to create any suitable fluid path using the structures of the present invention as described herein. A myriad of fluid paths 432, which may be at least partially collinear with each other or which may be completely separate, may extend through any bone preparation apparatus 414 in any suitable manner, and may be provided by one of ordinary skill in the art according to the teachings of the present invention.

Optionally, when the insertion structure (here, tubes 422) is in a penetrating relationship with the patient tissue, at least one fluid path 432 may be substantially separated laterally (i.e., in a lateral direction 428) from at least a portion of at least one other fluid path by intervening patient tissue. For example, and as shown in FIG. 4, there is patient tissue located laterally between adjacent ones of the tubes 422.

A fluid may be directed along the fluid path 432 to perform a patient tissue preparation task of any desired type. That is, a fluid such as, but not limited to, a gas (e.g., nitrogen), a relatively viscous liquid (e.g., bone cement), a relatively non-viscous liquid (e.g., saline), and/or a pressure gradient (e.g., a vacuum) could be directed in either direction along any one or more fluid paths 432 for any desired reason and under any desired amount of pressure. Optionally, relatively small particles of solid materials may be carried by a fluid—intentionally or incidentally—without destroying the "fluid" nature of the carrier material. It is also contemplated that antibiotics, chemotherapy drugs, or any other fluids having therapeutic functions could be delivered using the fluid path 432. Any bone preparation activities provided by the bone preparation apparatus 414 could be one-time and/or ongoing and may occur during or after the surgical procedure in which the bone preparation apparatus 414 is initially presented to the patient tissue.

Direction of any fluid along one or more fluid paths 432 can be controlled in any desired manner, including manually, semi-automatically, or automatically, and using any mechanical, electronic, or any other suitable control means (e.g., valves of any type or substantially equivalent technologies, controlled by the user in any suitable way). For example, a pump (not shown) may selectively passes one fluid into a selected portion of the bone preparation apparatus 414 while the same or another pump may selectively pass another type of fluid into a different part of the bone preparation apparatus. As another example, suction (i.e., a negative pressure gradient) can be selectively applied to any patient tissue(s), whether adjacent or spaced apart from each other, using an electronically controlled valve or any other means allowing suction and/or injection of fluid, either singly or in an alternating manner. As an example of operation of the present invention, fluid, such as pressurized saline or bone cement, could be controlled to flow in a first direction (e.g., from the fluid source toward the patient tissue) along a first fluid path 432 and could, for instance, perform the bone preparation tasks of rinsing and/or debriding the patient tissue (for the saline) or adhering a structure—e.g., the insertion structure—to the patient tissue (for the bone cement). A fluid—either the same or a different fluid—could be controlled to flow along the same or a different fluid path 432 in a second direction, which may be opposite the first direction, simultaneously or sequentially with the flow of the fluid along the first fluid path just described; for instance, a different fluid path could have a vacuum (i.e., a pressure gradient) flowing from the patient tissue toward a vacuum/fluid source, in order to suction away saline and tissue debris broken loose by the fluid flowing down the first fluid path.

Additionally, it is contemplated that, particularly for situations in which fluid is flowing away from the patient tissue, through a shell perforation 430, and into the interior cavity 424, the structure shell 426 may provide a "venting" function whereby the fluid is permitted to flow out of an outer surface of the insertion structure and not be directed into the manifold. One example of this "venting" use of the bone preparation apparatus 414 is when a gas is directed from a fluid source 434 through a first fluid path 432 toward the patient tissue to dry the patient tissue proximate to and/or contacting the insertion structure. The gas can then be "vented" through a second fluid path which is open to the ambient atmosphere surrounding at least a portion of the bone preparation apparatus 414 without entering the manifold 416. As another example, a bone cement could flow along a first fluid path 432 in the first direction, toward the patient tissue, at the same time that a curing agent, such as air or another gas, flows down a second fluid path in the first direction, the bone cement and curing agent meeting at a location proximate or contacting the patient tissue adjacent an inserted portion of the insertion structure. One of ordinary skill in the art can readily specify a fluid type(s), fluid source(s), flow direction(s), fluid path(s), and other desired properties for a particular use environment of the present invention.

An alternate arrangement of the bone preparation apparatus 414 of FIG. 4 is shown in FIG. 5. The bone preparation apparatus 414 of FIG. 5 depicts several optional features, each of which could also or instead be provided to the bone preparation apparatus 414 of FIG. 4. Unlike that shown in FIG. 4, the manifold 416 of FIG. 5 is recessed into a top of the bone 100 and is located beneath a covering plate 536, which may assist with the fluid connections described herein, such as by linking a fluid line 420 with the manifold and/or a tube 422. Each tube 422 in FIG. 5 has a 1:1 match with a corresponding fluid line 420, while multiple tubes 422 in FIG. 4 may share a fluid path 432 through the same fluid line 420. Additionally, the tubes 422 of FIG. 5 extend into the patient tissue to a depth which is shown in this Figure as being substantially uniform.

Figure 7:
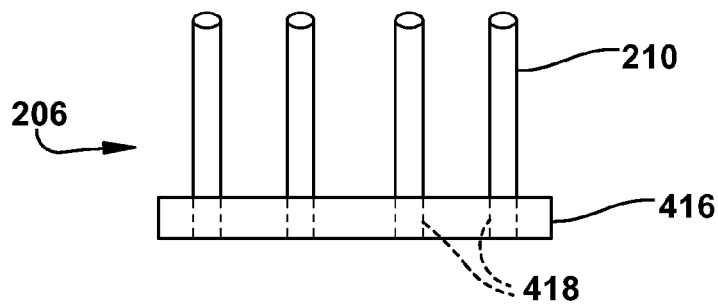
FIG. 7 is a side view of an embodiment of the present invention.
Figure 8:
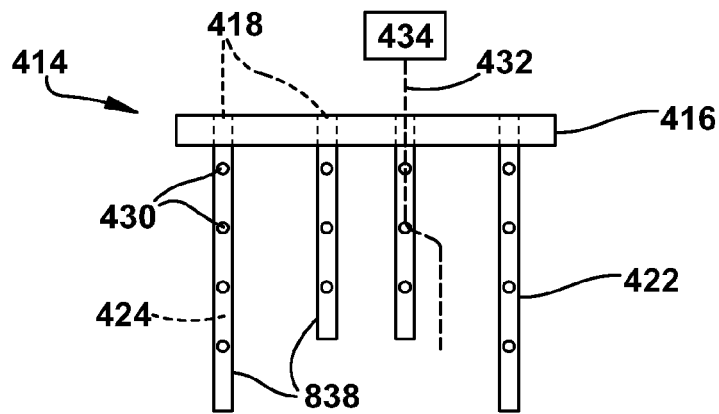
FIG. 8 is a side view of an embodiment of the present invention.

FIGS. 6-11 depict a bone preparation apparatus 414 and guide 206 in more detail than that shown in FIGS. 1-5. In FIGS. 6-11, the manifold 416 doubles as a guide plate 208. The manifold 416 is shown in plan view in FIG. 6, with a plurality of manifold apertures 418 present. In FIG. 7, guide tubes 210 have been inserted into some or all of the manifold apertures 418 for a fluid connection therewith and extend from the top of the manifold 416 to form a guide 206. The same manifold 416 is shown in FIG. 8 with tubes 422 inserted into some or all of the manifold apertures 418 for a fluid connection therewith and extending from the bottom of the manifold 416 to form a bone preparation apparatus 414. The guide tubes 210 and/or tubes 422 may be either permanently or removably attachable to the manifold 416—if the former, separate manifolds 416 may be used for the guide 206 and the bone preparation apparatus 414. For many, though not necessarily all, applications of the present invention, there will be direct correspondence between the number and locations of guide tubes 210 or other guiding devices used to prepare the cavities 312 and the number and locations of insertion structures 838, such as tubes 422, inserted into the patient tissue. One of ordinary skill in the art will realize that the manifold 416 shown in FIG. 6 need not also have guide plate 208 properties, however, and that separate structures (both of which may share some or all of the physical arrangement of components shown in FIG. 6) may be provided as separate guide plate and manifold structures.

Figure 9:
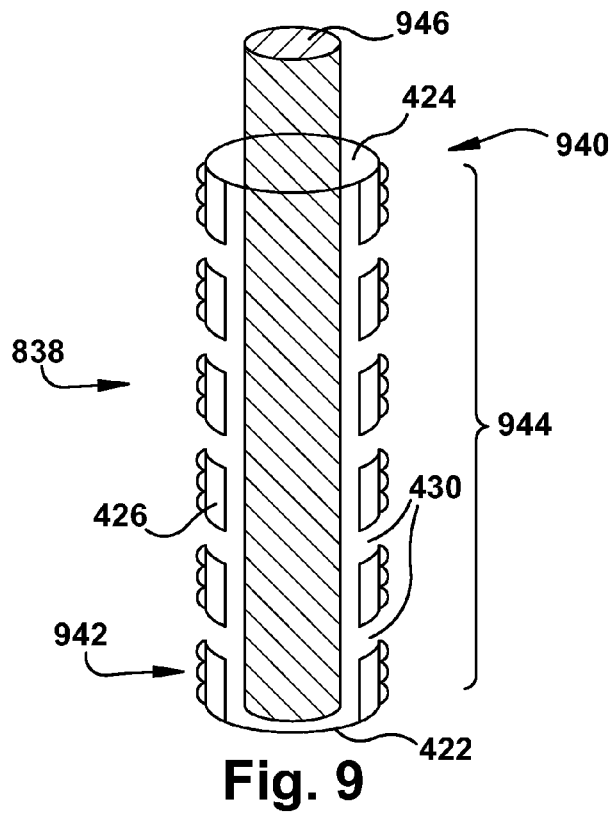
FIG. 9 is a side view of an embodiment of the present invention.
Figure 10:
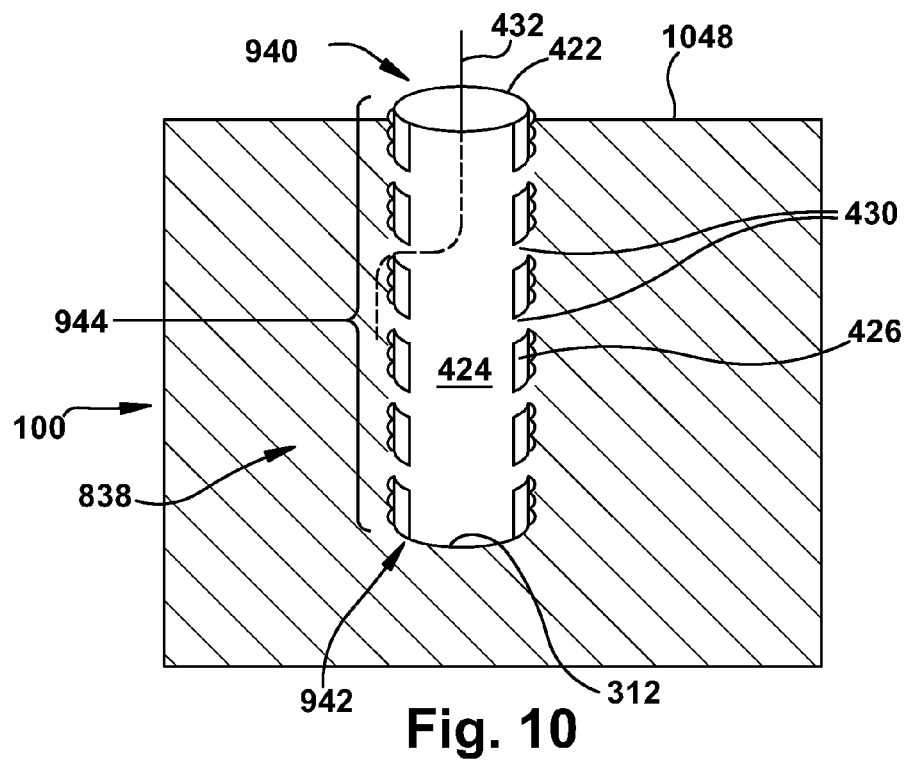
FIG. 10 is a side view of the embodiment of FIG. 9 in an example use environment.

An example embodiment of an insertion structure 838 is shown in detail in FIGS. 9 and 10. The depicted insertion structure 838 is of a round tube 422 type. The tube 422 has proximal and distal tube ends 940 and 942, respectively, separated by a tube body 944 defining at least a portion of the interior cavity 424. The tube body 944 can be considered to comprise the structure shell 426 here. The tube body 944 has at least one tube perforation therethrough serving as a shell perforation 430. Optionally, the distal tube end 942 may be "open" to the interior cavity 424 and may itself serve as a shell perforation 430.

A placement rod 946, or other relatively rigid structure corresponding physically with at least a portion of the interior cavity 424, may be inserted into the interior cavity as shown in FIG. 9 and may be used to stiffen or reinforce the insertion structure 838 during penetration of the insertion structure into the patient tissue. The placement rod 946 may be removed once the insertion structure 838 has achieved a desired penetrating, and optionally mating, relationship with the patient tissue, or the placement rod may instead be left in place and optionally used to facilitate the creation of a desired fluid path 432.

In FIG. 10, the tube 422 has been inserted into cavity 312 in the patient tissue 100. The cavity 312 may have been previously prepared for the tube 422, for example, by a predrill procedure. In other words, the patient tissue may be altered to accept in a mating relationship an insertion structure 838 having a particular physical configuration property (e.g., length, width, cross-sectional shape, orientation with respect to the patient tissue, or any other physical property) before the insertion structure is placed into the penetrating and mating relationship with the patient tissue. Alternatively or additionally, the insertion structure 838 itself could form at least a portion of the cavity 312 as the penetrating and mating relationship is being formed. For example, a relatively small-diameter "pilot" cavity 312 could be drilled into the patient tissue to facilitate penetration of a larger-diameter insertion structure 838 to some extent, while the insertion structure 838 forces the "pilot" cavity 312 to enlarge further during penetration.

With particular reference to FIG. 10, the tube 422 has achieved the penetrating and mating relationship with a bone 100 in any suitable manner, such that the distal tube end 942 has penetrated into the bone and at least one shell perforation 430 is located beneath an outer surface 1048 of the bone. The proximal tube end 940 has been placed in fluid communication with a fluid source (omitted from this Figure for clarity), either directly or through connection with a chosen manifold aperture (also omitted from this Figure for clarity). Accordingly, when the tube 422 type insertion structure 838 has achieved the position of FIG. 10 and the aforementioned connections have been made, a fluid path 432 extends through the manifold aperture 418, into the proximal tube end 940, through at least a portion of the tube body 944 (serving as the structure shell 426), through a shell perforation 430, and out of the interior cavity 424 into at least one of a proximate and contacting (here, the latter) relationship with the patient tissue (bone 100) beneath the outer surface 1048 thereof.

Figure 11:
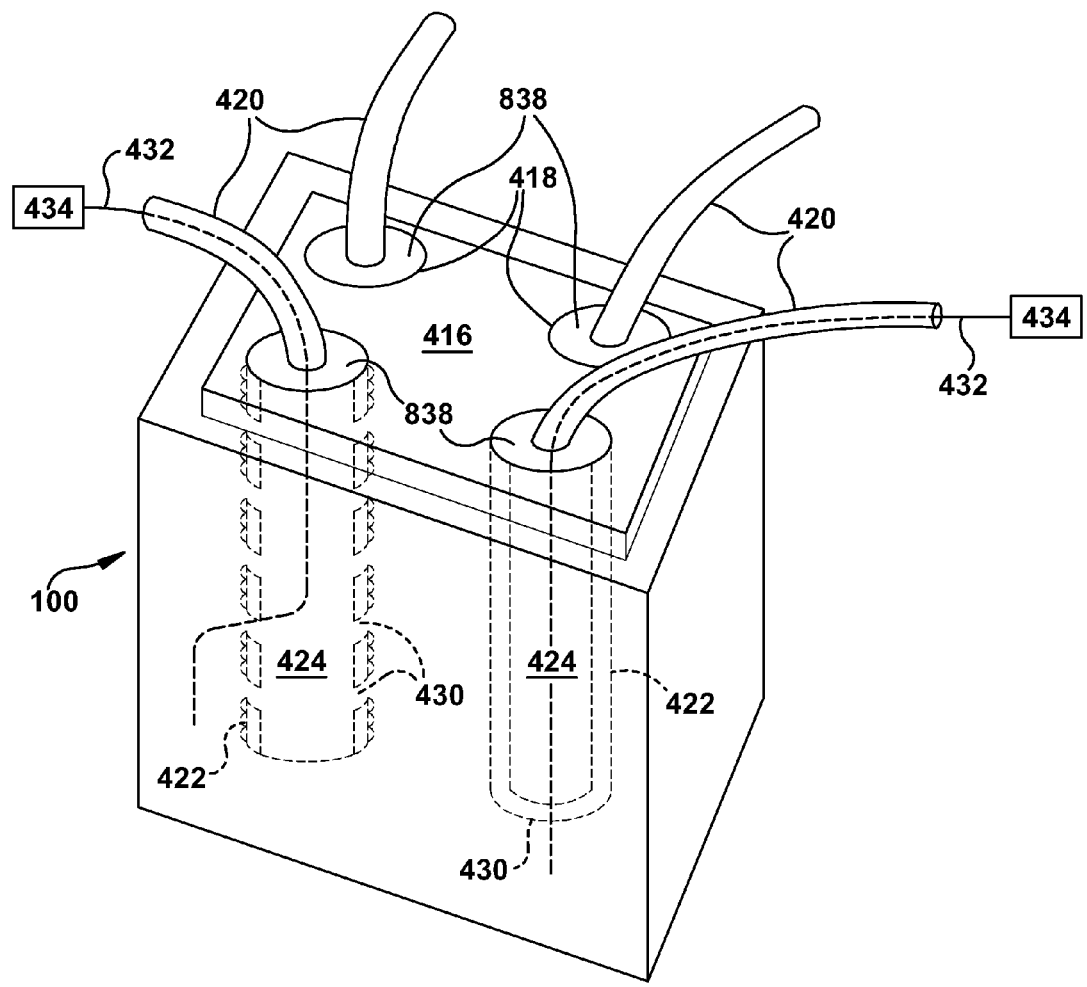
FIG. 11 is a perspective top view of an embodiment of the present invention.

FIG. 11 schematically depicts a perspective view of a bone preparation apparatus 414 having a plurality of insertion structures 838 of the tube 422 type. In this Figure, the manifold 426, manifold apertures 418, and fluid lines 420 can be clearly seen. The bone preparation apparatus has been inserted into a patient tissue of the bone 100 type and is ready for use in a bone preparation operation, in which fluid flows from one or more fluid sources 434, through corresponding fluid paths 432, and into at least one of a proximate and a contacting relationship with a portion of the patient tissue located beneath the outer surface 1048 thereof. As with any embodiment of the present invention, the structures comprising one or more of the fluid sources 434, manifolds 426, manifold apertures 418, fluid lines 420, and/or insertion structures 838, or any other structures of the bone preparation apparatus 414 may be separately provided from component parts attached together permanently or temporarily, or may be monolithically formed (i.e., formed or composed of material without joints or seams) in a unitary manner from a single piece of raw material.

Figure 12A:
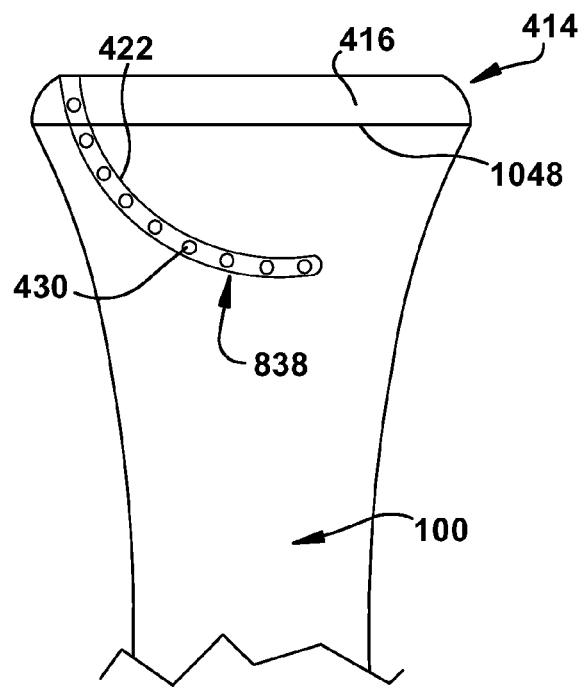
FIG. 12A is a side view of an embodiment of the present invention in an example use environment.
Figure 12B:
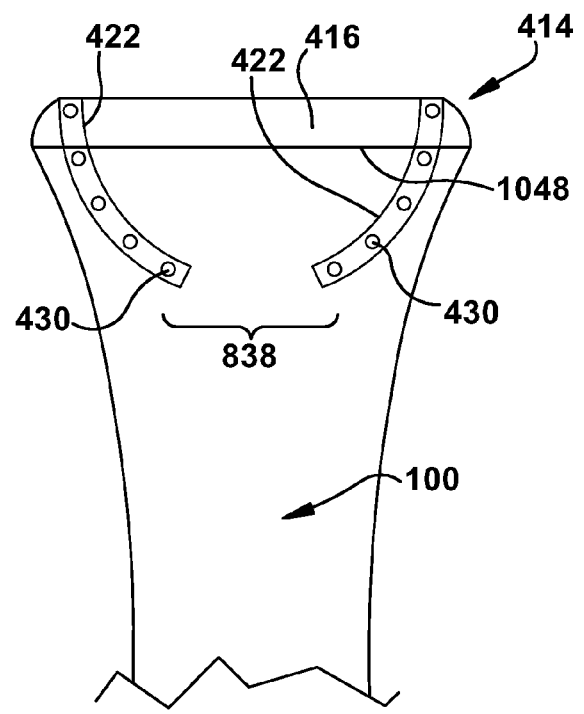
FIG. 12B is a side view of an embodiment of the present invention in the example use environment of FIG. 12A.
Figure 13A:
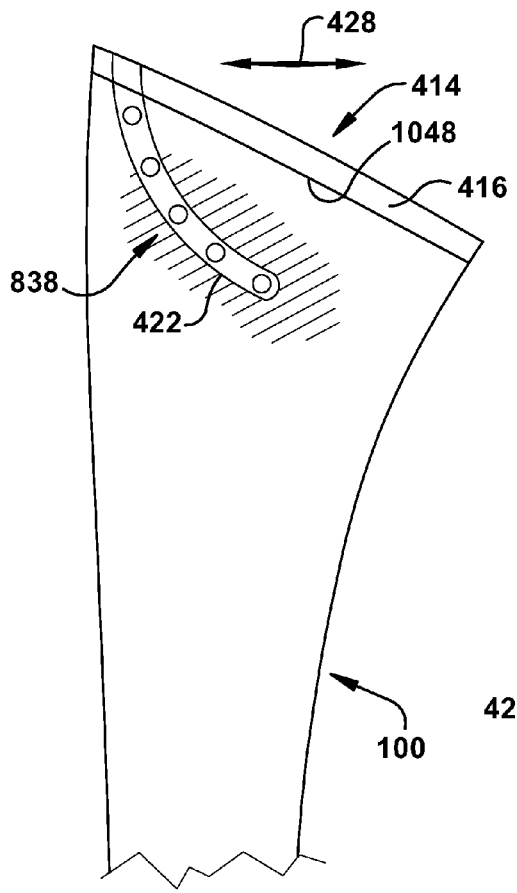
FIG. 13A is a side view of an embodiment of the present invention in an example use environment.
Figure 13B:
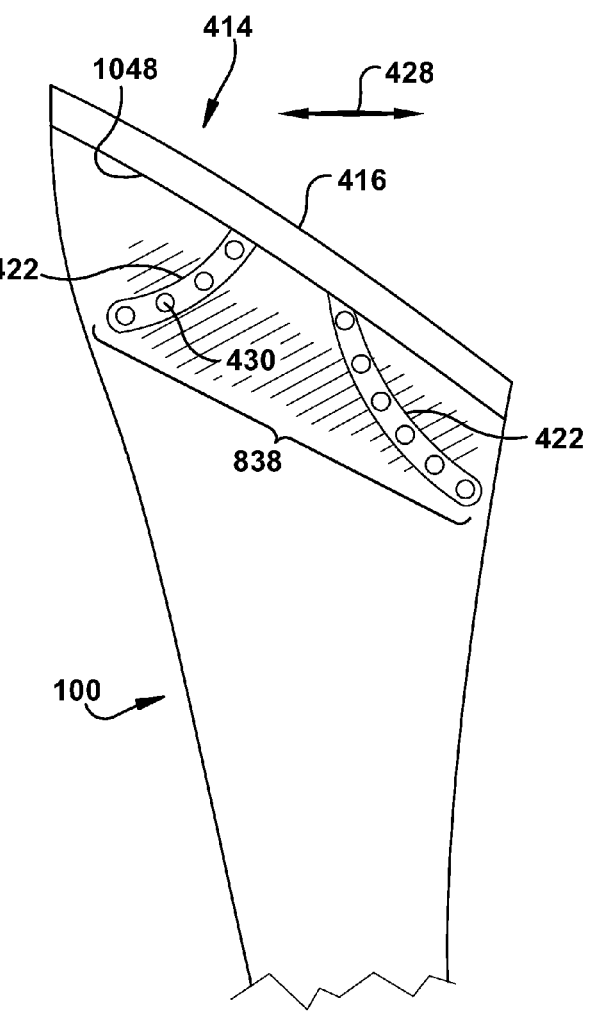
FIG. 13B is a side view of an embodiment of the present invention in the example use environment of FIG. 13A.

The insertion structures 838 may have any desired physical configuration properties. With reference to FIGS. 12A-13B, the insertion structures 838 may be curved tubes 422—or have any other suitable physical dimensions/profiles—and may be made of any suitable material, including but not limited to any metal, porous, bioabsorbable, or biocompatable material. The insertion structures 838 may penetrate in any desired direction into any portion of the patient tissue. For example, the insertion structure 838 in FIGS. 12A and 13A is a relatively long, curved tube 422. The insertion structures 838 of FIGS. 12B and 13B are two somewhat shorter tubes 422 than those of FIGS. 12A and 12B, but still have a substantially curved profile. In FIGS. 12A-13B, the manifold 416 is located atop a cut (flat) outer surface 1048 of a bone 100. The bone 100 in FIGS. 12A-12B is a tibia and the bone 100 in FIGS. 13A-13B is a humerus, though, as previously mentioned, the present invention can be used with any suitable bone or other patient tissue.

In FIG. 13A, the insertion structure 838 penetrates into the bone 100 beginning at a location relatively near a laterally outer perimeter of the cut outer surface 1048 of the bone (e.g., into cancellous bone, the approximate location of which is shown by the shading in this Figure, of the metaphysis). In FIG. 13B, the insertion structures 838 instead penetrate into the bone 100 beginning at locations relatively near a laterally central portion of the cut outer surface 1048 of the bone.

Figure 13C:
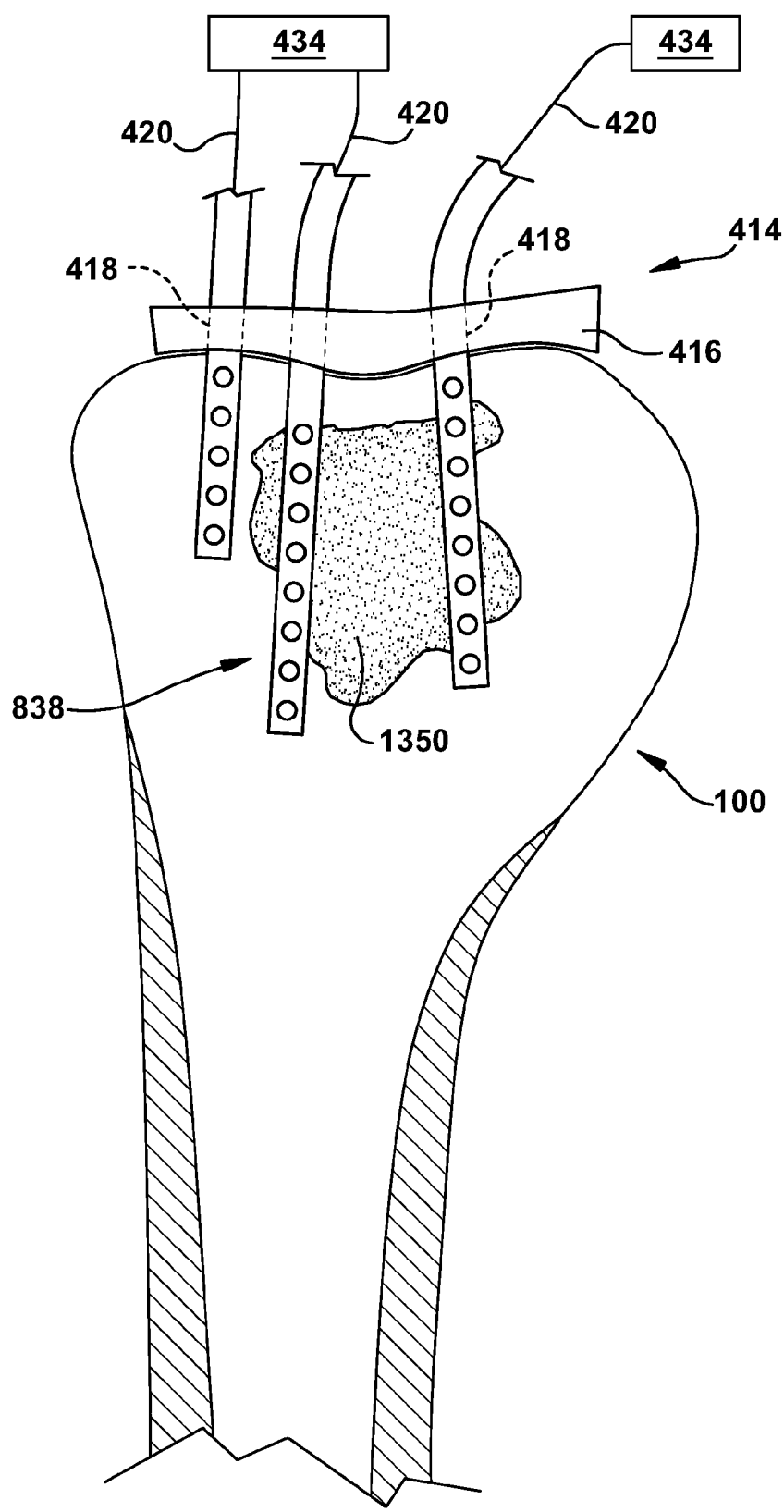
FIG. 13C is a side view of an embodiment of the present invention in the example use environment of FIG. 13A.

The insertion structures 838 may initially penetrate the bone 100 or other patient tissue at any suitable location on an outer surface 1048 thereof, whether or not the outer surface has been cut or otherwise machined during the surgical procedure. This is depicted schematically in FIG. 13C, in which a plurality of insertion structures 838 are schematically shown penetrating into different portions of a head of a bone 100 to perform bone preparation tasks throughout that entire area. More specifically, FIG. 13C depicts a bone 100 which includes a defect 1350, such as a tumor or other differentiated area of patient tissue. Optionally, defect 1350 may represent a void from which a tumor or other patient tissue has been removed. The bone preparation apparatus 414 shown in this Figure includes a plurality of insertion structures 838, some of which extend into and/or through the defect 1350. Via the bone preparation apparatus 414, fluid can be directed into the defect 1350 volume, optionally to at least partially fill that volume (when empty), and thereby enhance the structure of the surrounding patient tissue. The manifold 416 is optionally left in situ after conclusion of the surgical procedure. FIG. 13C also shows an optional fluid path 432 configuration, where multiple fluid sources 434 are provided to various of the insertion structures 838.

Figure 14:
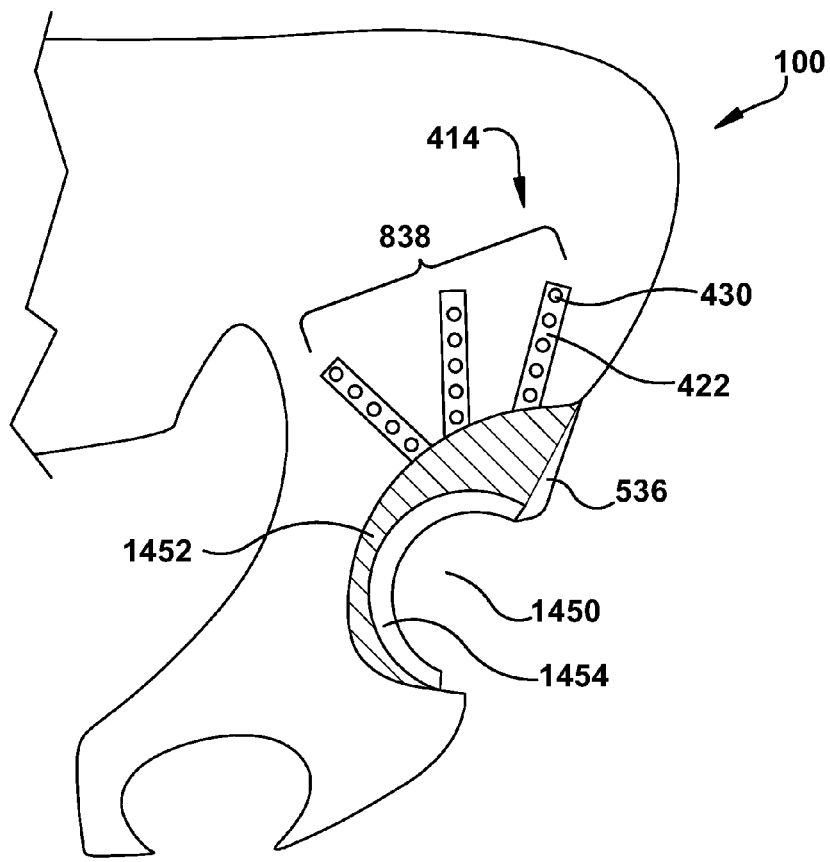
FIG. 14 is a side view of an embodiment of the present invention in an example use environment.
Figure 15A:
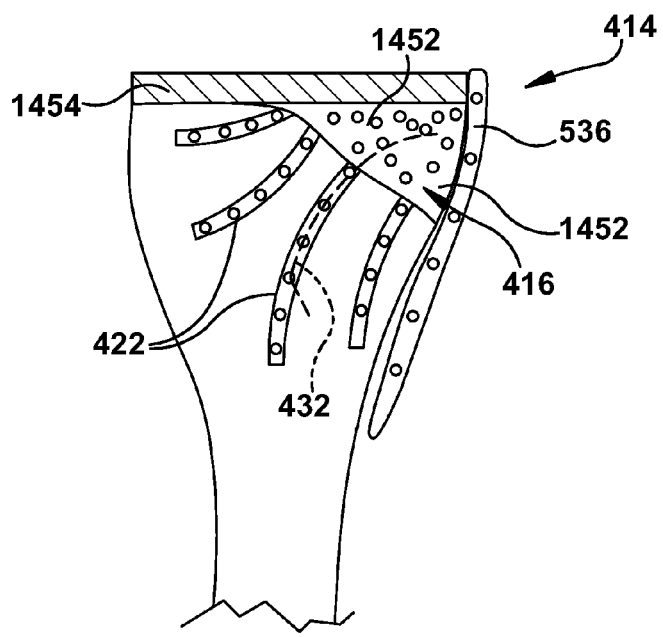
FIG. 15A is a side view of an embodiment of the present invention in an example use environment.
Figure 15B:
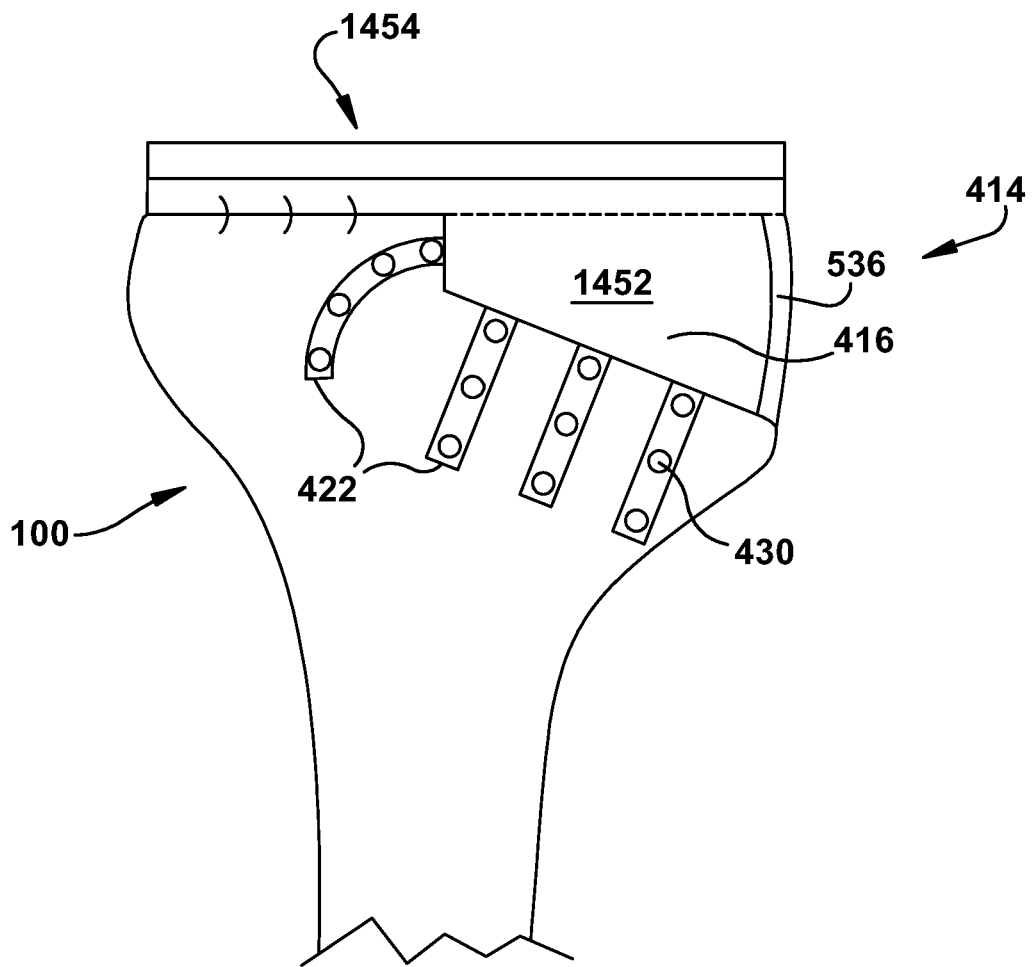
FIG. 15B is a side view of an embodiment of the present invention in the example use environment of FIG. 15A.
Figure 15C:
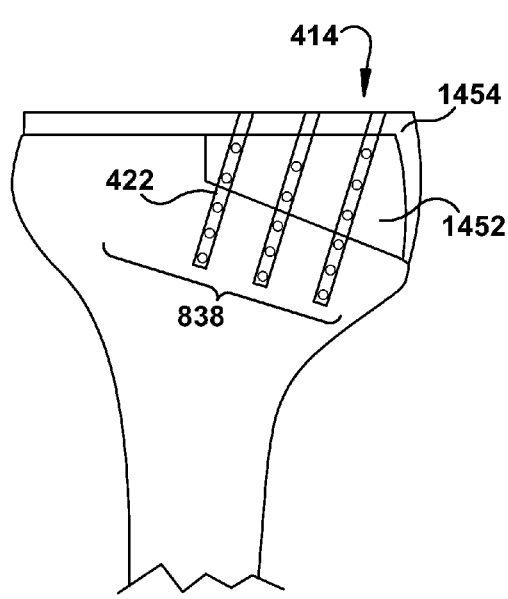
FIG. 15C is a side view of an embodiment of the present invention in the example use environment of FIG. 15A.
Figure 15D:
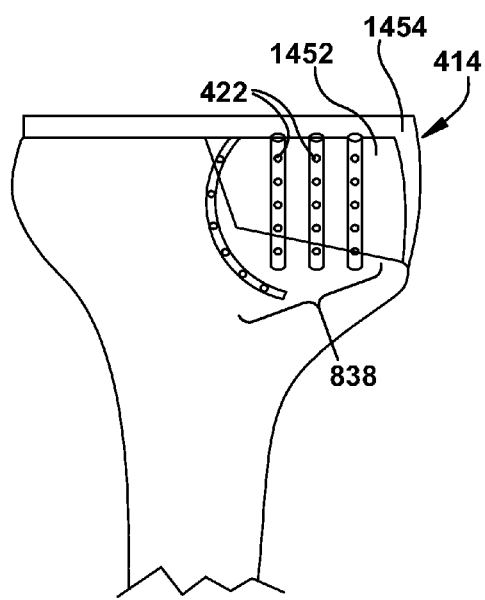
FIG. 15D is a side view of an embodiment of the present invention in the example use environment of FIG. 15A.
Figure 15E:
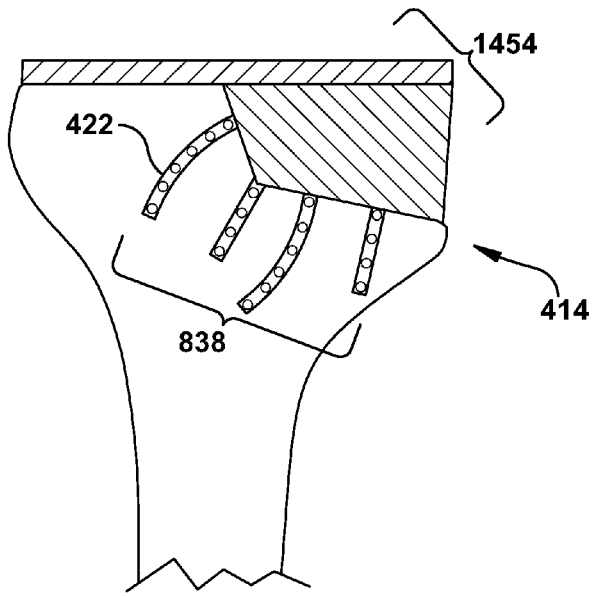
FIG. 15E is a side view of an embodiment of the present invention in the example use environment of FIG. 15A.

FIGS. 14-15E depict additional examples of embodiments of the present invention in various configurations and various use environments, and at various points in a surgical procedure. In FIG. 14, an acetabulum 1450 is depicted as including defective bone 1452 (the shaded area of FIG. 14). A prosthetic implant component 1454 (here, an acetabular cup) has been placed as desired and the defective bone 1452 was be backfilled (e.g., injected) with bone graft substitute, bone cement, and/or growth promoting material, or any other desired material, through use of the bone preparation apparatus 414. Additionally or alternately, the prosthetic implant component 1454 can be attached to the patient tissue through the use of a fluid provided by the same, or a different, bone preparation apparatus 414. Here, a bone preparation apparatus 414 has been used in a similar manner to that shown in FIGS. 1-4. The manifold 416 has been removed from the surgical site already in this view, and the tubes 422 are remaining at least semi-permanently inserted into the bone 100 at or near the site of the defective bone 1452. A cover plate 536 may be present (attached to or separate from the prosthetic implant component 1454) to act as a buttress plate and prevent the bone graft substitute, bone cement, and/or growth promoting material, or any other desired material from oozing out of the cavity 312 around the prosthetic implant component 1454. In this way, it is demonstrated that cancellous bone that is otherwise intact can be reinforced to support a graft or implant that is otherwise used to reconstruct the defect and/or joint surface, either by directly replacing or augmenting a native (potentially defective) structure.

FIG. 15A is similar to FIG. 14 in that a bone 100 (here, a tibia) has an area of defective bone 1452 which has been adjusted or reconfigured using a bone preparation apparatus 414. However, in FIG. 15A, the cover plate 536 is attached to, or part of, the prosthetic implant component 1454 (here, a tibia plate). Here, the tubes 422 are remaining in a penetrating relationship into the patient tissue adjacent the defective bone 1452, and fluid provided to the area of the defective bone 1452 has flowed along a fluid path 432 through the tubes 422 and into other portions of the bone 100.

FIG. 15B depicts a similar arrangement to that of FIG. 15A, with a slightly different arrangement for the cover plate 536 portion of the prosthetic implant component 1454. Likewise, FIGS. 15C-15E depict additional arrangements of previously emplaced and utilized components of a bone preparation apparatus 414, similar to of the final arrangement shown in FIG. 15A. In FIGS. 15C-15D, the tubes 422 extend through the prosthetic implant component 1454 and through the defective bone 1452 area, into another portion of the bone 100, with the insertion structures 838 extending through the defective bone 1452 area (which could have previously been at least partially filled with bone graft material). In FIG. 15E, the defective bone 1452 area itself has been excised and filled with a prosthetic implant component 1454, from which the tubes 422 or other insertion structures 838 extend into other portions of the bone 100. FIGS. 16-19 depict a bone preparation apparatus 414' according to a second embodiment of the present invention. The bone preparation apparatus 414' of FIGS. 16-19 is similar to the bone preparation apparatus 414 of FIGS. 1-15E and therefore, structures of FIGS. 16-19 that are the same as or similar to those described with reference to FIGS. 1-15E have the same reference numbers with the addition of a "prime" mark. Description of common elements and operation similar to those in the previously described first embodiment will not be repeated with respect to the second embodiment.

In the embodiment shown in FIGS. 16-19, a broach 1656, for example, a hollow shell broach, is depicted. Broach 1656 may have a hollow interior 1758. Broach 1656 may have shell perforations 430' on its outer surface and/or a solid center core 1760. Broach 1656 may be placed into a bone 100, for example, a long bone in which the metaphysis requires enhancement. The broach 1656 may be configured for engagement with a fluid source (not shown) via manifold 416' and/or may be directly attachable to the fluid source. The broach may be connectable to a broach impactor (not shown) through broach hole 1762, which may include a taper. The broach impactor may be used to position broach 1656.

By connecting broach 1656 to a fluid source, broach 1656 may serve as at least an insertion structure 838' of a bone preparation apparatus 414' and thereby perform at least one bone preparation task in a surgical environment. Broach 1656 may be positioned in bone 100, for example, in a cavity 312' of an intramedullary canal of a tibia or femur. Broach 1656 may be connected to a fluid source, optionally via a manifold (not shown), through use of a taper (i.e. Morse taper), screw, thread, locking mechanism, slip fit, interference fit, press fit, adhesive, bondable material, any combination thereof, or any other suitable connecting means. The fluid source may apply suction (i.e., a negative pressure gradient) to broach 1656 to remove excess or unwanted tissue and materials from the cavity 312'. Additionally, the fluid source may inject (i.e., with a positive pressure gradient) fixation material, therapeutic substance, or any other fluid into the cavity 312' via a fluid path (e.g., 432') extending through the broach 1656.

Broach 1656 may be removable after its use for bone preparation is over, or may be left in position for use as a semi-permanent final prosthetic implant component 1454'. ("Semi-permanent" is used herein to indicate that such a structure remains in the patient tissue after conclusion of the surgical procedure, regardless of how long such maintenance is intended to last and whether or not the structure was originally designed for such maintenance. Some examples of semi-permanent structures include replacement/artificial joint components and resurfacing joint components, whether trials for temporary use by the patient or intended to last some portion or all of the rest of the patient's life.)

That is, when the broach 1656 is acting as a removable component of a bone preparation apparatus 414', the insertion structure 838' of the broach is temporarily placed into a penetrating relationship below the outer surface 1048 of the patient tissue during the surgical procedure and is removed from the penetrating relationship before the surgical procedure ends. When the broach 1656 is serving as a temporary bone preparation tool and later removed, a standard prosthetic implant component (not shown) can be placed in the space of the patient tissue vacated by the removed broach. Alternatively, another permanent bone preparation apparatus 414 (as shown in FIG. 21-32 or 42A-45 and discussed below) can be inserted as an at least semi-permanent device having the capacity for additional bone preparation functions, which may be similar to those discussed above with reference to FIGS. 1-5.

Conversely, when the broach 1656 is acting as at least a portion of a semi-permanent final prosthetic implant component 1454', the insertion structure 838' of the broach is at least semi-permanently placed into a penetrating relationship below the outer surface 1048 of the patient tissue during the surgical procedure and remains in the penetrating relationship after the surgical procedure ends. These removable and semi-permanent characteristics/properties apply where appropriate for any embodiment of the present invention, not just the broach 1656 of the second embodiment. If broach 1656 is configured as at least a portion of a final prosthetic implant component 1454', broach is optionally connectable to an arthroplasty component.

As an example of a semi-permanent use of a bone preparation apparatus 414 in a short- or medium-term patient use (whether or not intended for a limited time), a revision procedure may be required at some time after the initial surgical procedure, for example, when broach 1656 is used as a final prosthetic implant component 1454'. The arthroplasty component (not shown) attached to the broach 1454' may be removed and/or the fluid source (not shown) may be reconnected to the broach 1656, with or without an intervening manifold. By reconnecting the fluid source, suction may be applied to the patient tissue 100 proximate or contacting the outer surface of the broach 1656 to remove excess or unwanted tissue and other debris/materials. Additionally, a fixation material, therapeutic substance, and/or other fluid may be provided to the patient tissue via the previously implanted broach 1656 as an insertion structure 838. A new, or the same, arthroplasty component may be reconnected to the broach 1656 at the end of the revision procedure.

Figures 20A, 20B:
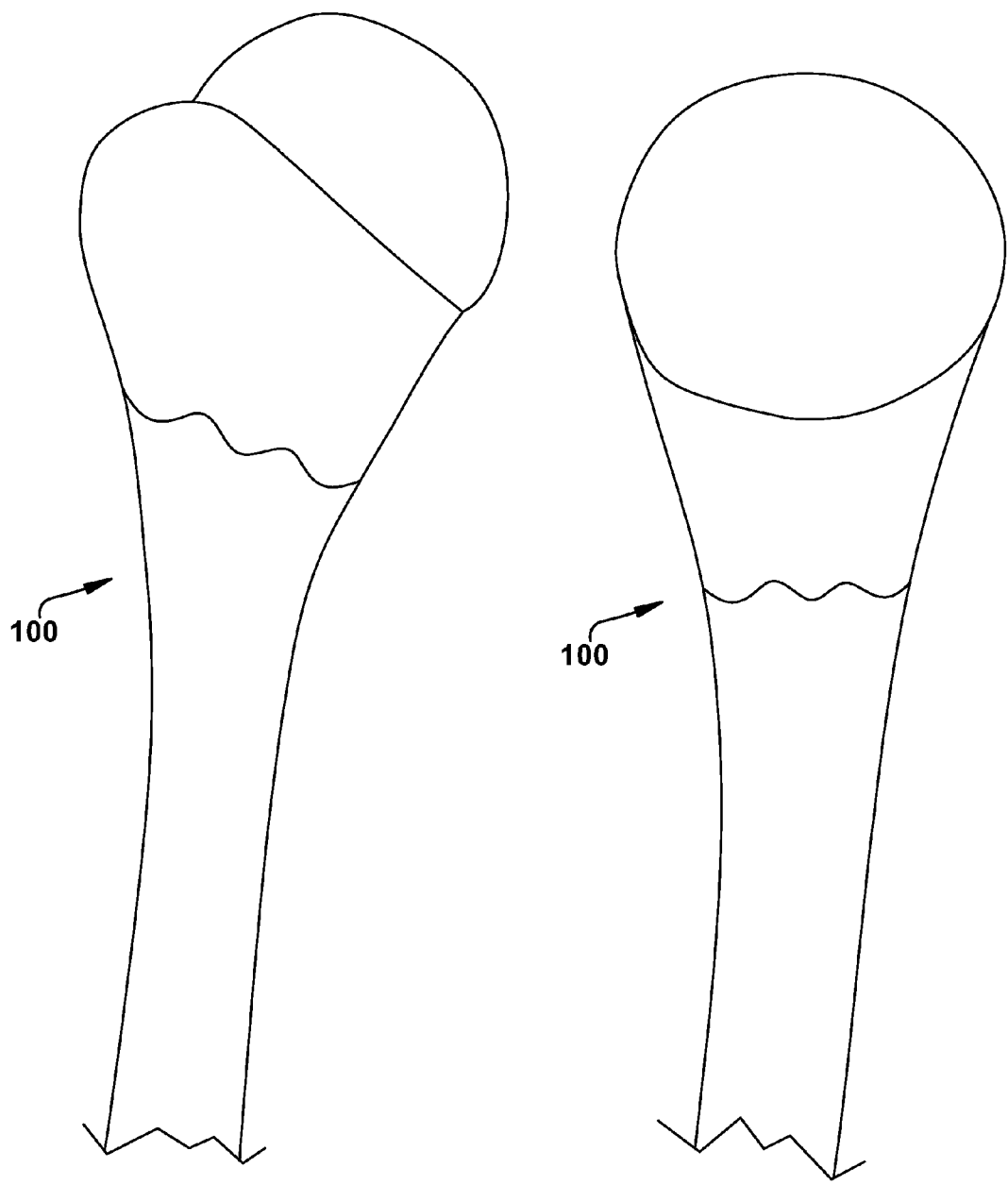
FIG. 20A is a first side view of an example use environment for the present invention.
FIG. 20B is a second side view of the example use environment of FIG. 20A.

Bone preparation and enhancement may also be performed using broaches, trial implants, or final implants as insertion structures 838'. Referring to FIGS. 20A and 20B, a typical long bone 100 includes a cortical diaphysis (lower region shown), cancellous metaphysis (middle region shown) and epiphysis (upper region shown). FIG. 20B shows the bone 100 after removal of the epiphysis (e.g., a humeral head) from the bone version depicted in FIG. 20A.

FIGS. 21-25 depict a bone preparation apparatus 414" according to a third embodiment of the present invention. The bone preparation apparatus 414" of FIGS. 21-25 is similar to the bone preparation apparatus 414 of FIGS. 1-15E and therefore, structures of FIGS. 21-25 that are the same as or similar to those described with reference to FIGS. 1-15E have the same reference numbers with the addition of a double "prime" mark. Description of common elements and operation similar to those in the previously described first embodiment will not be repeated with respect to the third embodiment.

Referring to FIGS. 21-25, embodiments may include a series of perforated tubes or plates as a trial prosthetic implant component 1454", broach 1656", or other tool (hereafter all presumed to be covered by the term "prosthetic implant component"), or as a final prosthetic implant component 1454". A "trial" prosthetic implant component 1454" is configured to be placed temporarily and then removed before the end of a surgical procedure. A "final" prosthetic implant component 1454" is configured to be left in the patient at least semi-permanently after completion of a surgical procedure. The trial or final prosthetic implant component 1454" may include at least one shell perforation 430". The trial or final prosthetic implant component 1454" may be at least partially embeddable into a patient tissue (e.g., bone 100" tissue such as cancellous bone). The trial or final prosthetic implant component 1454" may be configured to serve as all or part of a bone preparation apparatus 414", and as such, may be connectable to a fluid source 434" for creation of a fluid path 432" between the fluid source and a patient tissue.

Figures 21, 22:
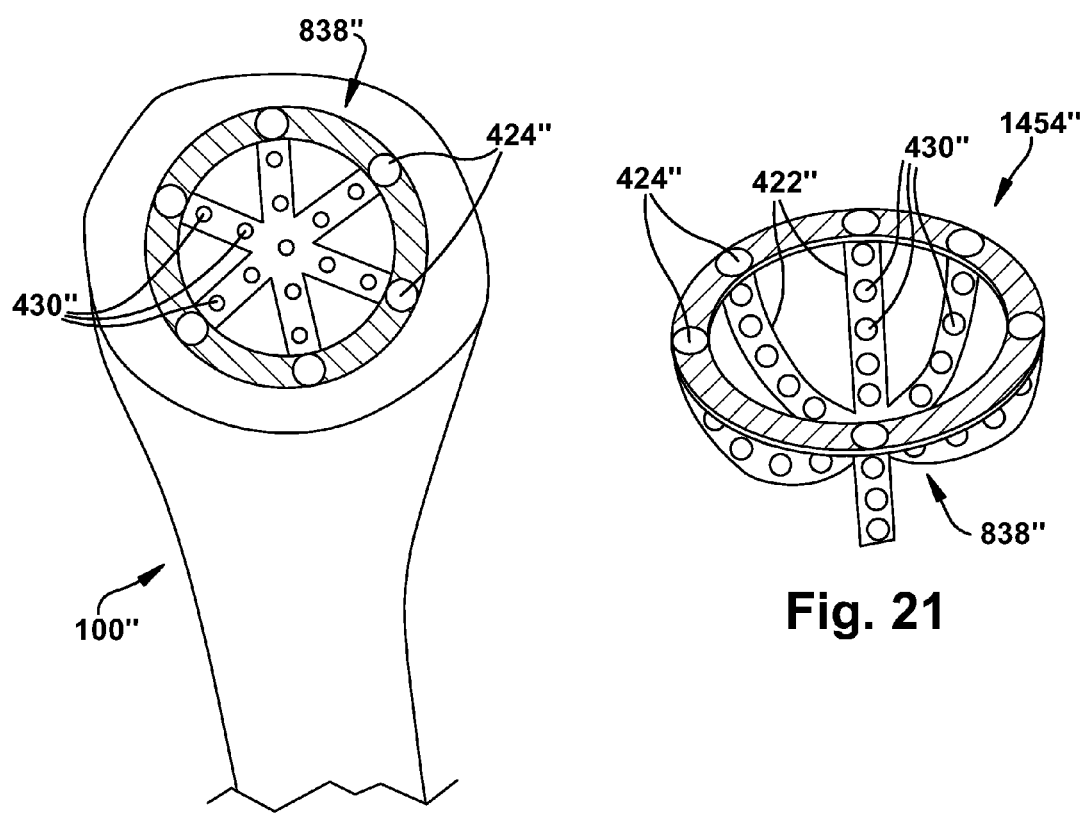
FIG. 21 is a top perspective view of an embodiment of the present invention.
FIG. 22 is a top perspective view of the embodiment of FIG. 21 in the example use environment of FIG. 20B.

For example, the prosthetic implant component 1454" shown in FIG. 21 includes an insertion structure 838" having a partispherical configuration. The depicted prosthetic implant component 1454" may be inserted into a cut outer surface 1048" of a humerus, as shown schematically in plan view in FIG. 22 and in side view in FIG. 23. Optionally, the outer surface 1048" of the humerus may have been machined (e.g., using a partispherical reamer, not shown) to include a cavity 312" for accepting the prosthetic implant component 1454", serving here as a bone preparation apparatus 414", in a mating and penetrating relationship.

Figures 23, 24, 25:
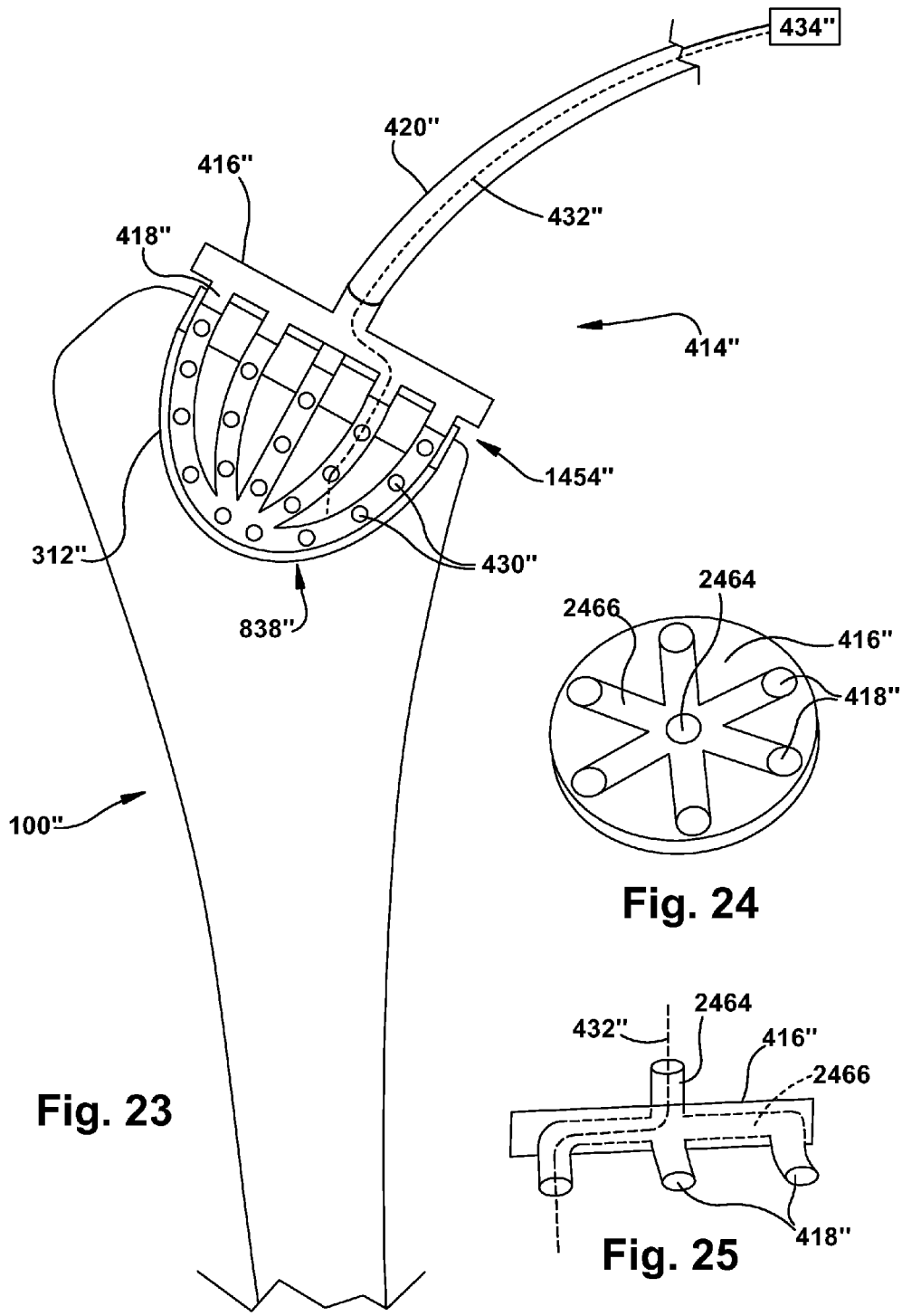
FIG. 23 is a side view showing the embodiment of FIG. 21 in the use environment of FIG. 20B.
FIG. 24 is a bottom view of an example configuration of a component of an embodiment of the present invention.
FIG. 25 is a bottom view of an example configuration of a component of an embodiment of the present invention.
Figure 26:
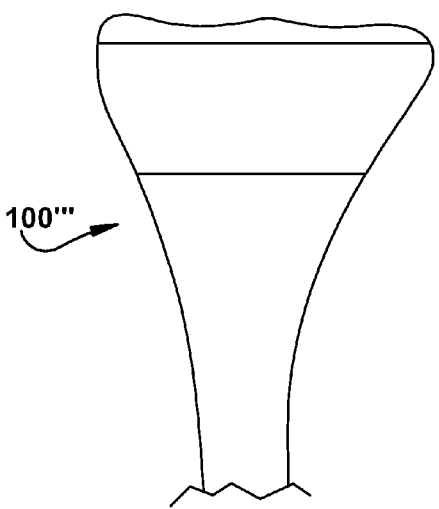
FIG. 26 is a side view of an example use environment for the present invention.

FIGS. 24 and 25 depict bottom views of example manifolds 416" which can be associated with the prosthetic implant component 1454" to form a bone preparation apparatus 414". In FIG. 24, the manifold 416" includes a central aperture 2464 for connection to a fluid source 434" (directly or through one or more fluid lines 420"). The central aperture 2464 then directs fluid to the manifold apertures 418" through an internal manifold channel 2466 (here, an asterisk-shaped construct). In FIG. 25, the internal manifold channel 2466 has a linear profile.

FIGS. 26-30 depict a bone preparation apparatus 414''' according to a fourth embodiment of the present invention. The bone preparation apparatus 414''' of FIGS. 26-30 is similar to the bone preparation apparatus 414 of FIGS. 1-15E and therefore, structures of FIGS. 26-30 that are the same as or similar to those described with reference to FIGS. 1-15E have the same reference numbers with the addition of a triple "prime" mark. Description of common elements and operation similar to those in the previously described first embodiment will not be repeated with respect to the fourth embodiment.

Optionally, the insertion structure 838''' may include multiple components or subassemblies which can themselves be inserted into a penetrating, and optionally mating, relationship with a cavity 312''' in a patient tissue. FIGS. 26-29 depict a tibial bone 100''' use environment, with a humeral use environment shown in FIG. 30, for a bone preparation apparatus 414''' according to the fourth embodiment of the present invention. As shown in these Figures, the bone preparation apparatus 414''' has an insertion structure 838''' comprising an insertion core 2768 and one or more (three shown) insertion fins 2770; the insertion core and/or insertion fins may be provided as a part of the insertion structure or may be separately provided. Optionally, the insertion fins 2770 may be attached to an insertion collar 2772 for connection to the insertion core 2768 and/or a manifold 416''' or other means of conveying fluid from a fluid source 434''' to the shell perforations 430'''. In FIGS. 26-29, this attachment is made via a threaded, screw-type connection. However, the insertion fins 2770 and insertion core 2768 may have any suitable attachment mechanism—or none at all, when these components are not attached together—and may be readily provided by one of ordinary skill in the art for a particular application of the present invention.

Optionally, and as shown in FIG. 29, the insertion core 2768 may include a hollow stem which acts as an interior cavity 424'''. Using a hollow insertion core 2768, a variety of fluid paths 432''' can be created to allow fluid access to/from many different areas of the cavity 312'''/312A''' and the patient tissue near the bone preparation apparatus 414'''. The hollow stem or any other interior cavity 424''' may be filled with any desired substance (e.g., bone cement, metal rod, or any other suitable filler) after the bone preparations tasks have been completed. A filled stem or other interior cavity 424''' may be helpful in providing structural stability, for example, when the insertion structure 838''' is left at least semi-permanently within the patient tissue.

Figure 27:
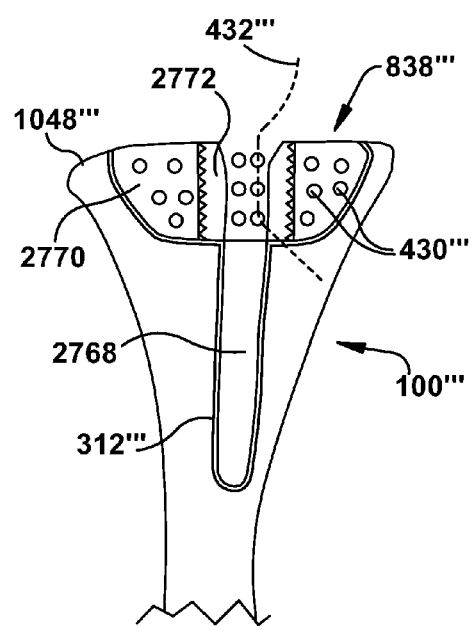
FIG. 27 is a side view of an embodiment of the present invention in the example use environment of FIG. 26.
Figure 28:
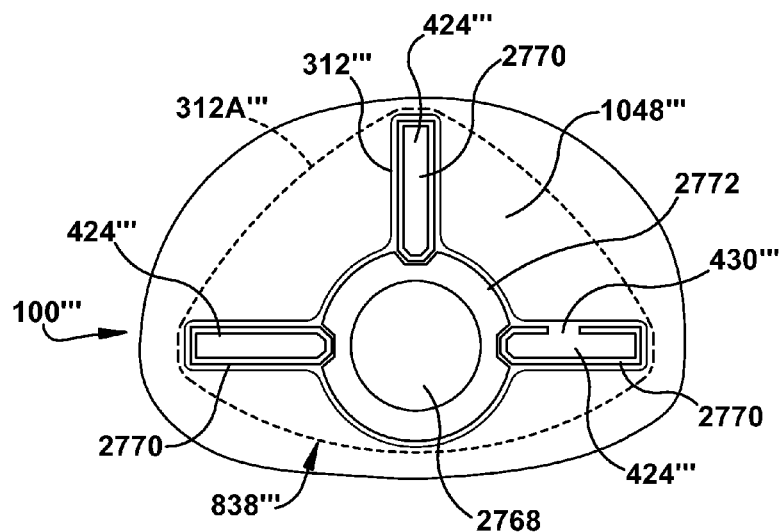
FIG. 28 is a top view of the embodiment of FIG. 27 in the example use environment of FIG. 26.

As shown in FIGS. 27-28, a shaped cavity 312''' may be provided to closely accept the insertion structure 838''' in a relatively close mating relationship. Alternatively, a more generically configured cavity 312A''' (shown in dashed line in FIG. 28) may be created to accept the insertion structure 838''' in a less-close mating relationship. Any desired material may be provided—though is not necessarily present—in any suitable manner to fill the portions of the generic cavity 312A''' which are not occupied by the insertion structure 838'''.

In the embodiment of the bone preparation apparatus 414''' shown in FIGS. 27-28, the insertion structure(s) 838''' may be placed into a penetrating relationship with the patient tissue by being inserted into a prepared cavity 312''' of any desired shape. Alternatively or additionally, at least a portion of the insertion structure(s) 838''' may be inserted into the patient tissue with no prepared cavity 312''', such that the insertion structure 838''' forms its own cavity as it enters the patient tissue under some amount of force.

A broach (not shown), other tools, or a trial or final prosthetic implant component 1454''' can be used to provide one or more fluid paths 432''' into a cavity 312''' in the patient tissue. The fluid path(s) 432''' can then be used to direct any desired flowable substance into the cavity 312''', optionally to help with fixation of the prosthetic implant component 1454''' in the patient tissue. For example, bone cement can be directed along the flow path within the bone preparation apparatus 414''' and into at least a portion of the surrounding cavity 312'''. Optionally, the bone cement can be provided under sufficient pressure to penetrate some distance into the patient tissue surrounding the bone preparation apparatus 414'''.

Particularly when the bone preparation apparatus 414''' doubles as a portion of a prosthetic implant component 1454''', the bone preparation apparatus can be held in place while the bone cement flows therethrough and cures, such that the bone cement functions to adhere the bone preparation apparatus in place mechanically and/or chemically. Alternatively, the bone preparation apparatus 414''' may be at least partially removed from the patient tissue once the fluid (e.g., bone cement) has been provided within the cavity 312''' and a prosthetic implant component 1454''' may be inserted in place of the bone preparation apparatus for affixation by the previously placed bone cement.

Alternatively, the cavity 312''', possibly with fluid contained therein, could be left unfilled to close naturally or could be closed by a surgeon with no structure (such as an implant or tool) located therein. Optionally, an insertion structure 838''' which has been cemented into place can be used as a base or anchor for attachment to a separately provided portion of a prosthetic implant component 1454''', as shown in FIGS. 29-30.

The above example uses affixation of a prosthetic implant component 1454''' to a cavity 312''' using bone cement as a fluid, but any desired bone preparation task(s) can be carried out during/after a surgical procedure, using any desired fluid (s), for any reason. As another example of a suitable bone preparation task, the bone preparation apparatus 414''' may be used to provide pressurized saline to a cavity 312''' and may also be used to simultaneously or sequentially supply a suction pressure gradient to remove the saline and included patient tissue debris from the cavity 312'''.

FIG. 30 shows a bone preparation apparatus 414''' similar to that of FIGS. 26-29, except that the bone preparation apparatus of FIG. 30 is used with a humeral prosthetic implant component 1454''', rather than the tibial prosthetic implant component of FIGS. 26-29.

Figure 32:
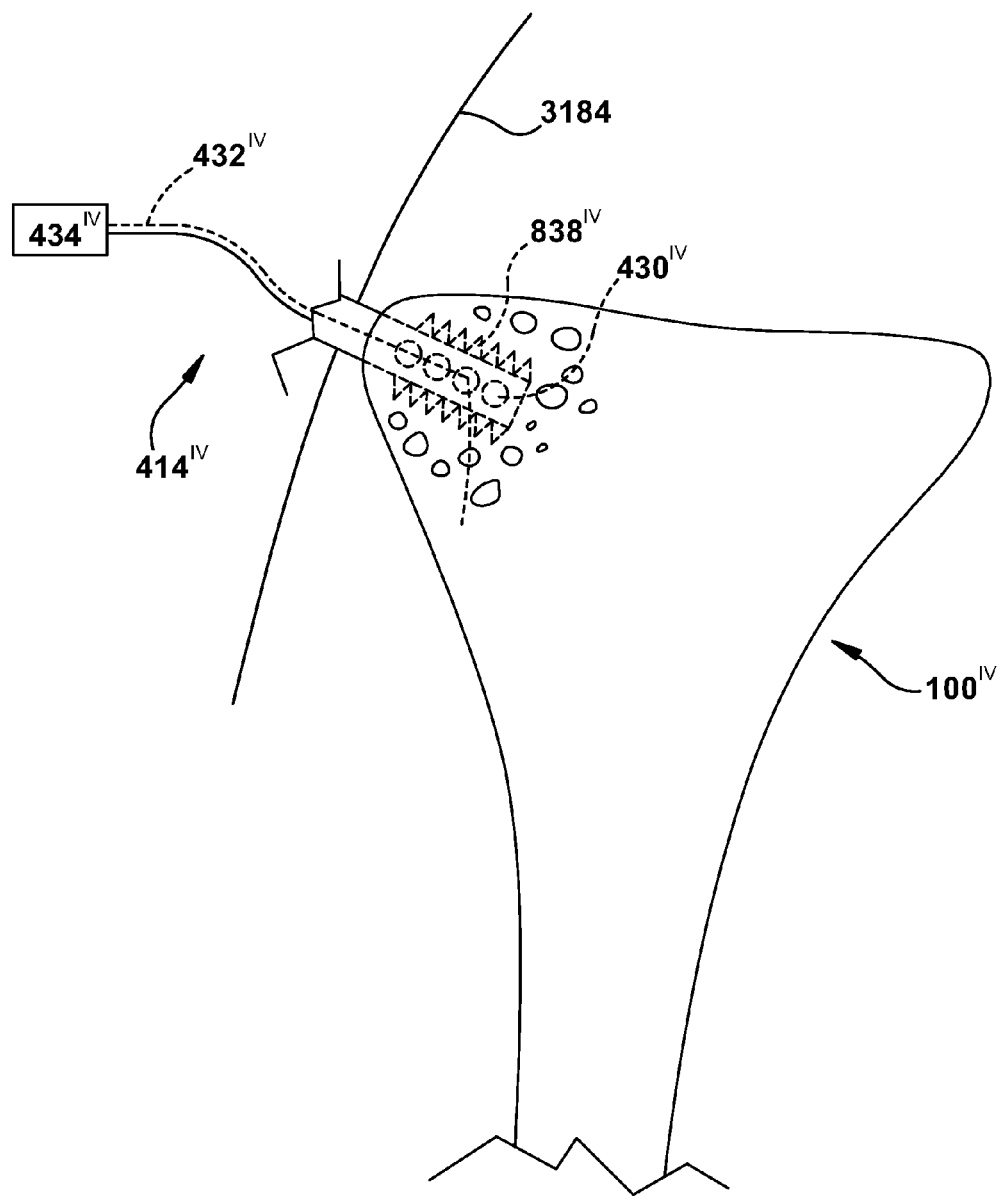
FIG. 32 is a side view of an embodiment of the present invention in an example use environment.
Figure 33:
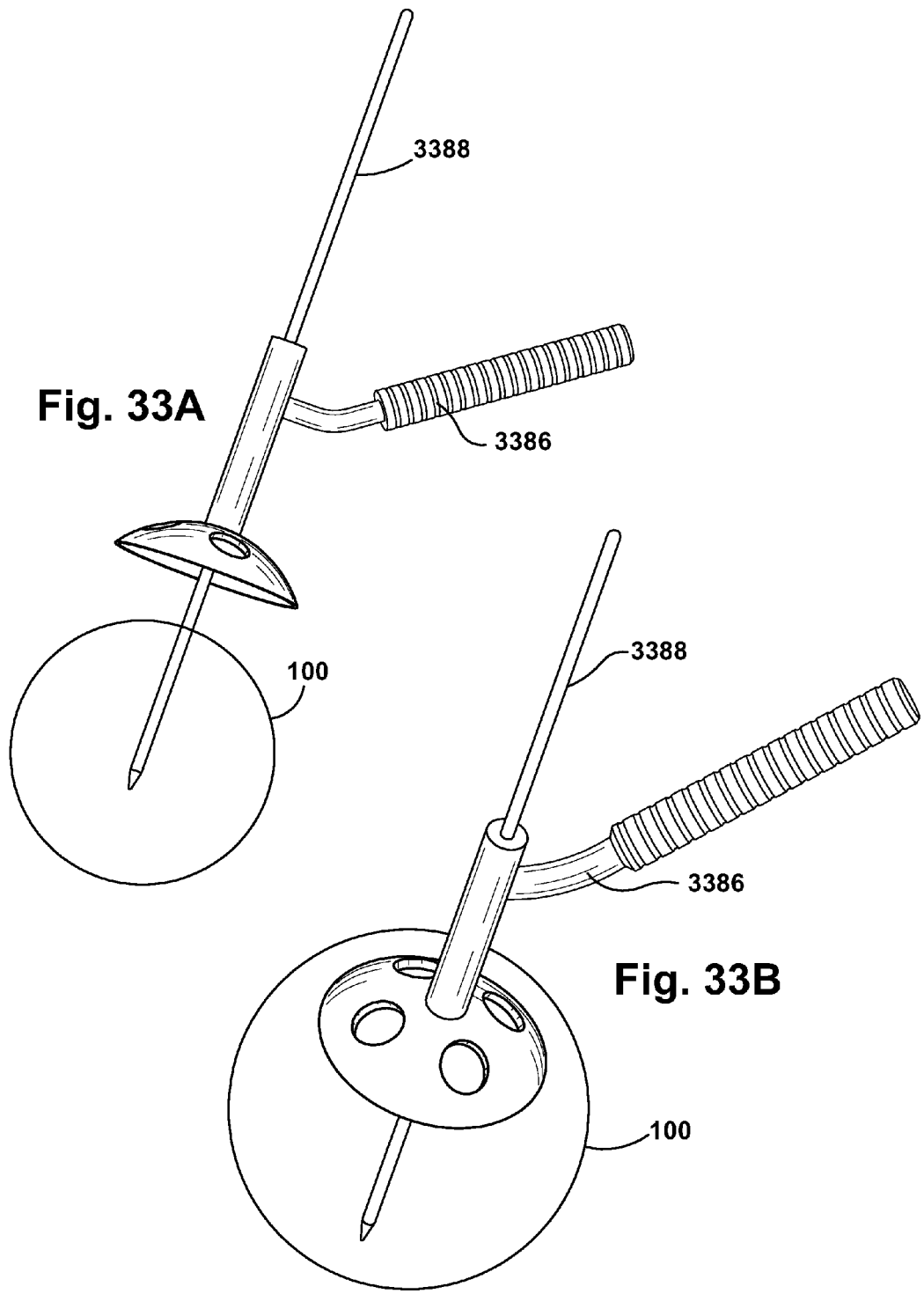
FIG. 33A is a side view of a tool for use with an embodiment of the present invention.
FIG. 33B is a top perspective view of the tool of FIG. 33A.

FIGS. 31-32 depict a bone preparation apparatus $414^{iv}$ according to a fifth embodiment of the present invention. The bone preparation apparatus $414^{iv}$ of FIGS. 31-32 is similar to the bone preparation apparatus 414 of FIGS. 1-15E and therefore, structures of FIGS. 31-32 that are the same as or similar to those described with reference to FIGS. 1-15E have the same reference numbers with the addition of a Roman numeral "iv" superscript. Description of common elements and operation similar to those in the previously described first embodiment will not be repeated with respect to the fifth embodiment.

FIG. 31 depicts a plurality of bone preparation apparatus $414^{iv}$ which can be used as anchors within the bone $100^{iv}$ or other patient tissue. For example, one or more bone plates 3174 can be attached to the bone $100^{iv}$ using an inserted screw 3176 having bone preparation apparatus $414^{iv}$ features. The screw 3176A is attached to a remotely located fluid source $434^{iv}$ by a fluid line $420^{iv}$, optionally through a remotely located manifold ($416^{iv}$, omitted from this Figure). The screw 3176B is directly connected to a proximate fluid source $434^{iv}$ that is secured to, and steadied with, the bone plate 3174 by use of seal 3178—for example, the proximate fluid source $434^{iv}$ may be a flexible reservoir that is squeezed to direct fluid through fluid line $420^{iv}$ and into the interior cavity $424^{iv}$ of the insertion structure $838^{iv}$. The screw 3176C is driven into the bone $100^{iv}$ using a driver 3180, which may have a cannulated shaft 3182. Optionally, a fluid source $434^{iv}$ may be placed in fluid communication with the cannulated shaft 3182 to direct fluid therethrough—thus using the cannulated shaft as a fluid line $420^{iv}$—and into the screw 3176C for provision to the associated cavity $312^{iv}$.

FIG. 32 depicts an insertion structure $838^{iv}$ which takes the form of a suture anchor. The suture anchor type insertion structure $838^{iv}$ may include a thread, cannulation, and/or perforation, any of which may be configured for use as a shell perforation $430^{iv}$ to help provide a fluid path $434^{iv}$ for provision of fluid from a fluid source $434^{iv}$ to patient tissue, such as cancellous bone surrounding the insertion structure $838^{iv}$. For example, bone cement could be pumped into the bone $100^{iv}$ to assist with affixation of the suture anchor and thereby help resist pullout of the suture anchor under force from an attached suture thread 3184.

Embodiments of the present invention may include devices and instruments for implantation and/or application-specific preparation of the patient tissue site. Embodiments may include suction and/or irrigation for partial or complete removal of the marrow contents, which may include areas adjacent to the prosthetic implant component 1454. The application of fixation material or any other fluid used with a bone preparation apparatus 414 may be selected based on the area of the body, the patient's treatment site, the type of the prosthetic implant component 1454 to be used, or any other desired selection factors. This allows selection of an appropriate prosthetic implant component 1454 and/or method to fit the patient conditions and/or type of procedure, for example, based on bone condition, condition of a joint replacement, type of fracture fixation, type of reconstruction, or any other patient tissue condition(s).

FIGS. 33A-45 depict an example embodiment of a bone preparation apparatus 414 according to any embodiment of the present invention, along with multiple tools, devices, instruments, and the like which can be used for application-specific preparation of the patient tissue and implantation of a trial or final prosthetic implant component 1454, of which the bone preparation apparatus 414 comprises a portion.

In FIGS. 33A-45, patient tissue, such as cancellous or another type of bone 100 may be prepared by using a custom or stock cutting tool, osteotome, and/or power burr to create a cavity 312 in the bone configured for the shape and/or dimensions of a bone preparation apparatus 414, for example, a suction, irrigation and/or injection bone preparation apparatus. A pin guide 3386, such as that shown in FIGS. 33A-33B, can be used to help set a guide pin 3388 into underlying bone 100—here, a convex portion of a humeral head shown schematically—at a predetermined location and trajectory. Once placed, the guide pin 3388 can remain in the bone 100 to help guide the user in later steps of the surgical procedure.

Figure 34:
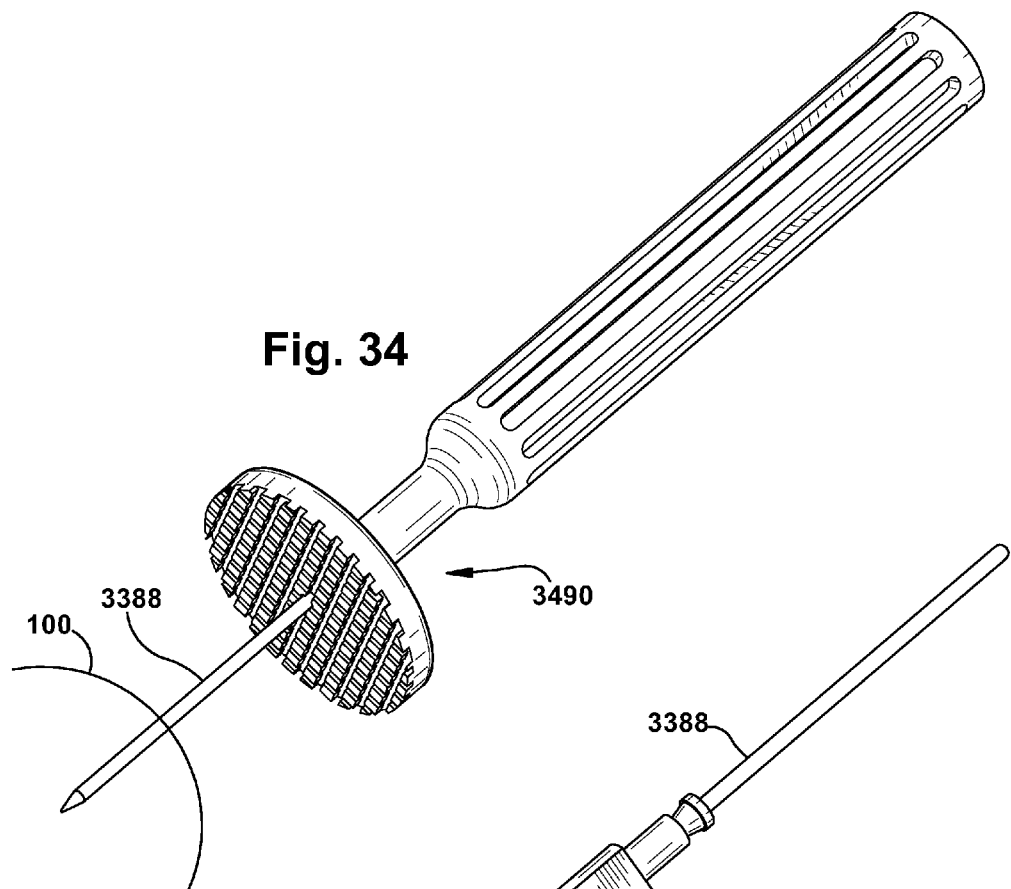
FIG. 34 is a side perspective view of a tool for use with an embodiment of the present invention.

FIG. 34 shows a manual reamer 3490 which is cannulated to fit over the guide pin 3388 and be guided thereby into machining contact with the bone 100. The manual reamer 3490 is used to flatten an outer surface 1048 of the bone 100 into the shape shown schematically in FIG. 34, and then the manual reamer is removed from the surgical site while the guide pin 3388 remains.

Figure 35:
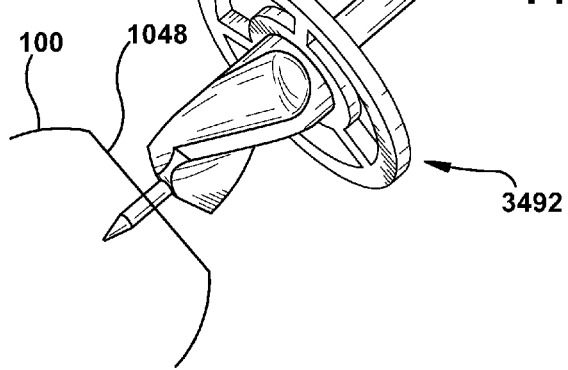
FIG. 35 is a side perspective view of a tool for use with an embodiment of the present invention.

In FIG. 35, a cannulated central drill 3592 is optionally guided toward the bone 100 (specifically, the flatted outer surface 1048 thereof) to drill a guide hole 3694 in the bone. Once the guide hole 3694 is drilled, a plug 3696 may be placed into the hole to help guide later steps of the surgical procedure with a more robust anchored structure (i.e., the plug) than the guide pin 3388 provides. The guide pin 3388 may remain in the bone 100, as shown in FIG. 36, along with the plug 3696, if desired. Alternately, the guide pin 3388 itself may do all of the guiding functions without the guide hole 3694 and plug 3696.

Figure 37B:
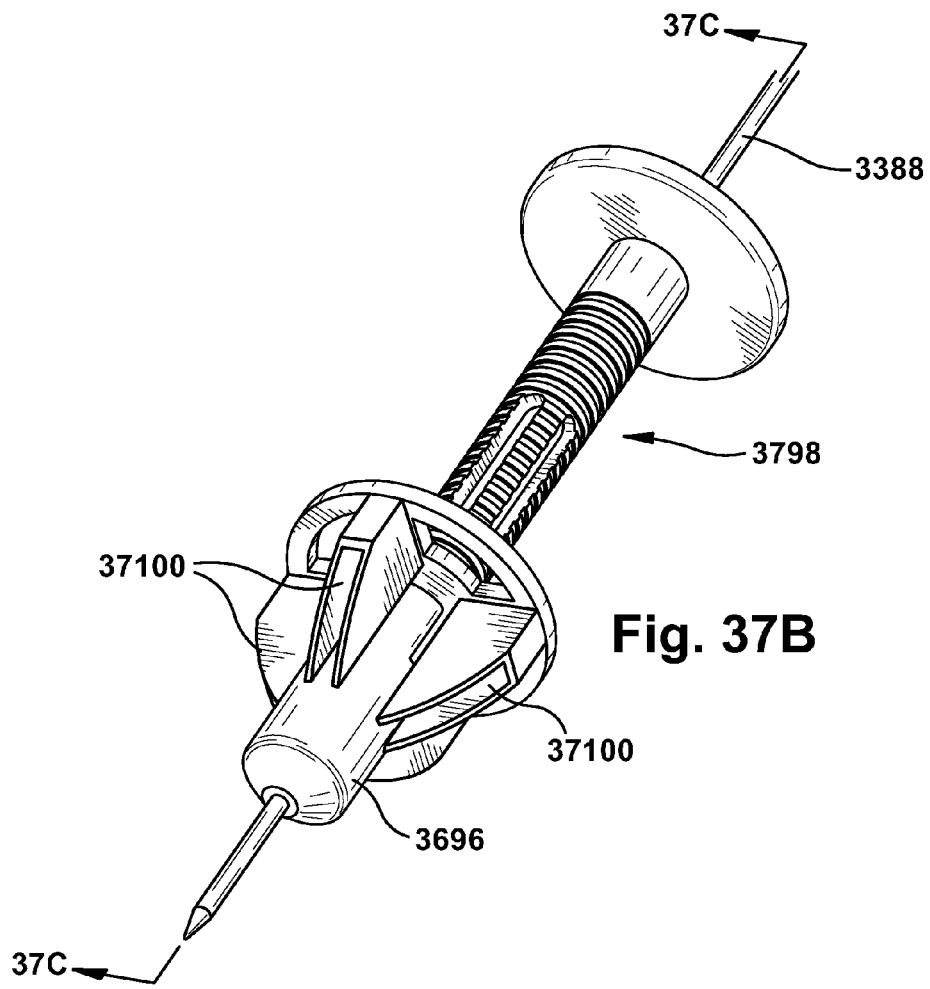
FIG. 37B is a perspective bottom view of the tool of FIG. 37A.
Figure 37C:
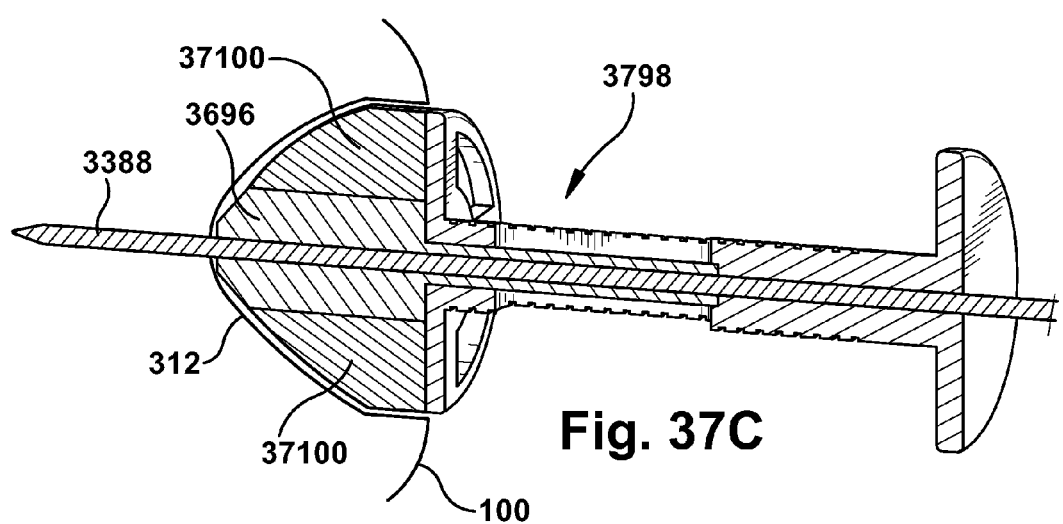
FIG. 37C is a cross-sectional view taken along line C-C of FIG. 37B.

FIGS. 37A-37C show a box osteotome 3798 which has a plurality of fin cutters 37100 to help create a cavity 312 having a cruciform profile. The box osteotome 3798 is cannulated and is slid over the guide pin 3388, until reaching a "hard stop" engagement with the plug 3696, in the arrangement shown in FIG. 37C.

Figure 38A:
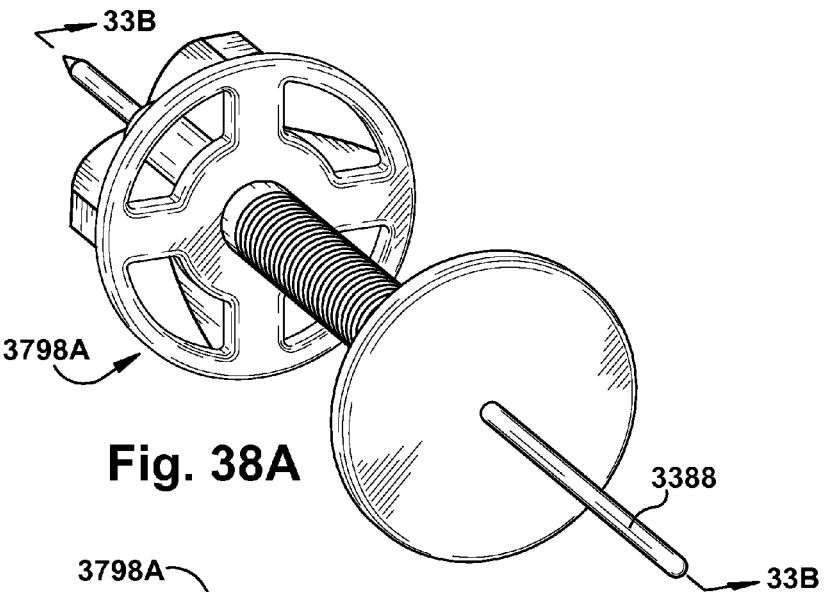
FIG. 38A is a top perspective view of an alternate configuration of the tool of FIG. 37A.
Figure 38B:
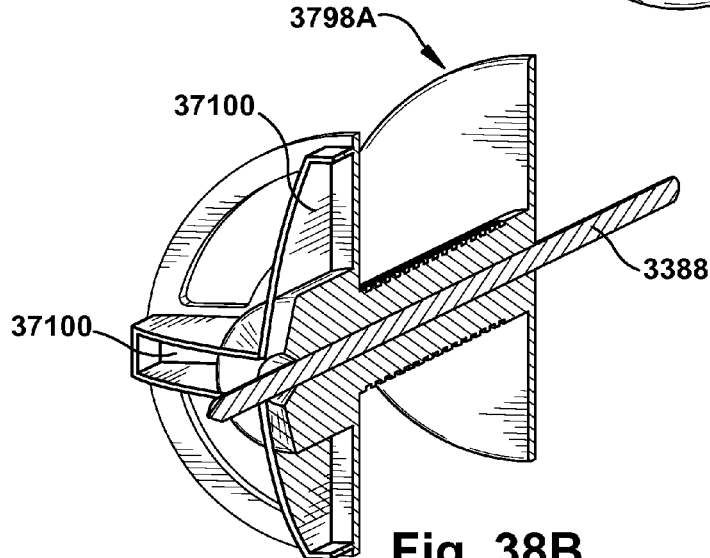
FIG. 38B is a cross-sectional view taken along line B-B of FIG. 38A.
Figure 38C:
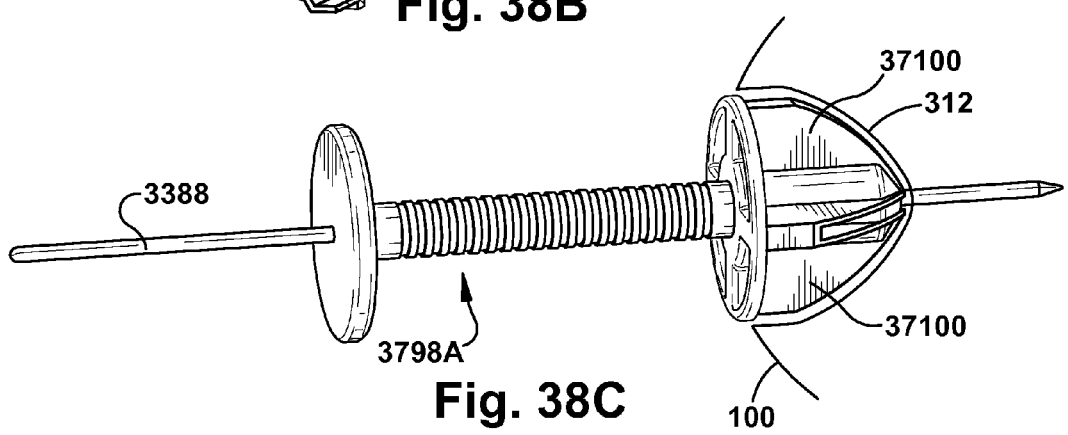
FIG. 38C is a side view of the tool of FIG. 38A.

FIGS. 38A-38C depict an alternate arrangement of a box osteotome 3798A, which incorporates a plug feature—for this embodiment, the plug 3696 is omitted (though the guide hole 3694 may still be present) and the box osteotome is guided into the bone 100 to create the cavity 312, as shown in FIG. 38C, through sliding engagement with the guide pin 3388.

Figure 39A:
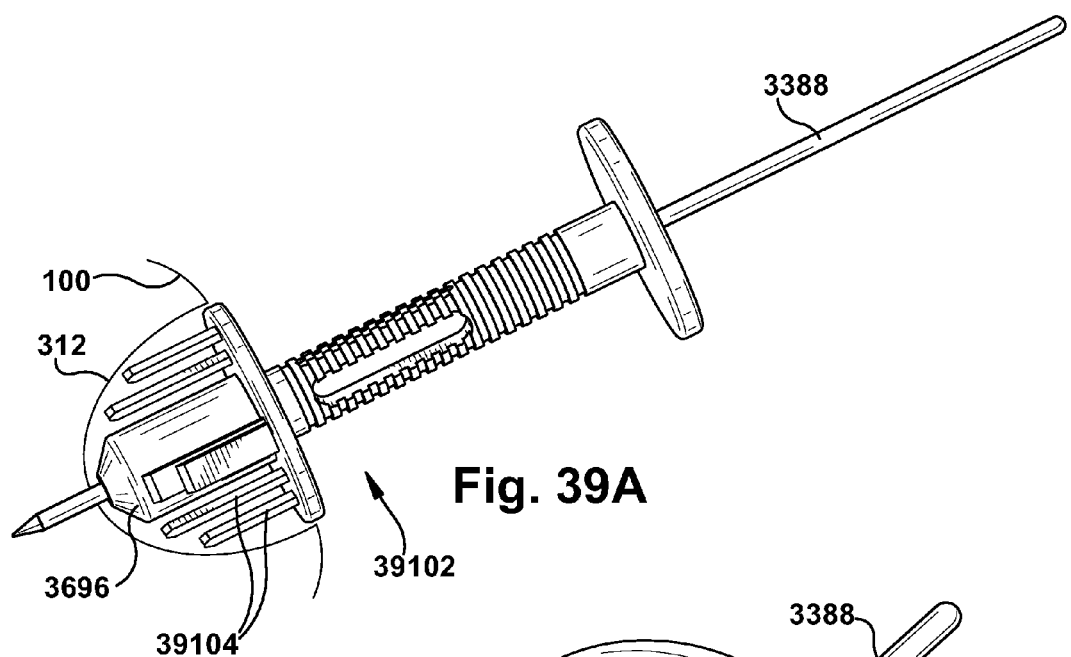
FIG. 39A is a side view of a tool for use with an embodiment of the present invention.
Figure 39B:
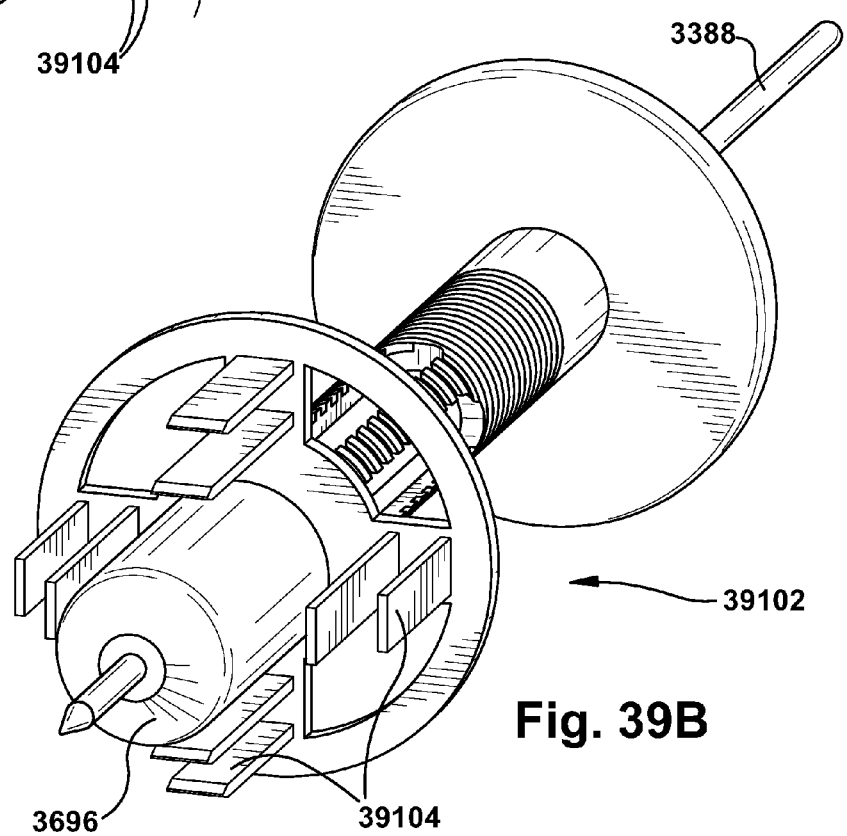
FIG. 39B is a bottom perspective view of the tool of FIG. 39A.

An eight-blade osteotome 39102 is shown in FIGS. 39A-39B. Similar to the box osteotome 3798, the eight-blade osteotome 39102 is guided into cutting contact with the bone by the guide pin 3388. This cutting contact should be oriented so that the cutter blades 39104 of the eight-blade osteotome penetrate into the portions of the bone 100 which have already been cut into and weakened by the fin cutters 37100 of the box osteotome 3798. The cutter blades 39104 will help morselize the bone 100 or other patient tissue in those previously weakened areas for sharper definition of the edges of the cavity 312 and easier removal of the patient tissue debris from the cavity. The straight osteotome 40106 and/or curved osteotome 40108, shown in FIGS. 40A and 40B, respectively, can be used in a known manner to further clean up and define the edges of the cavity 318.

Figures 40A, 40B, 41:
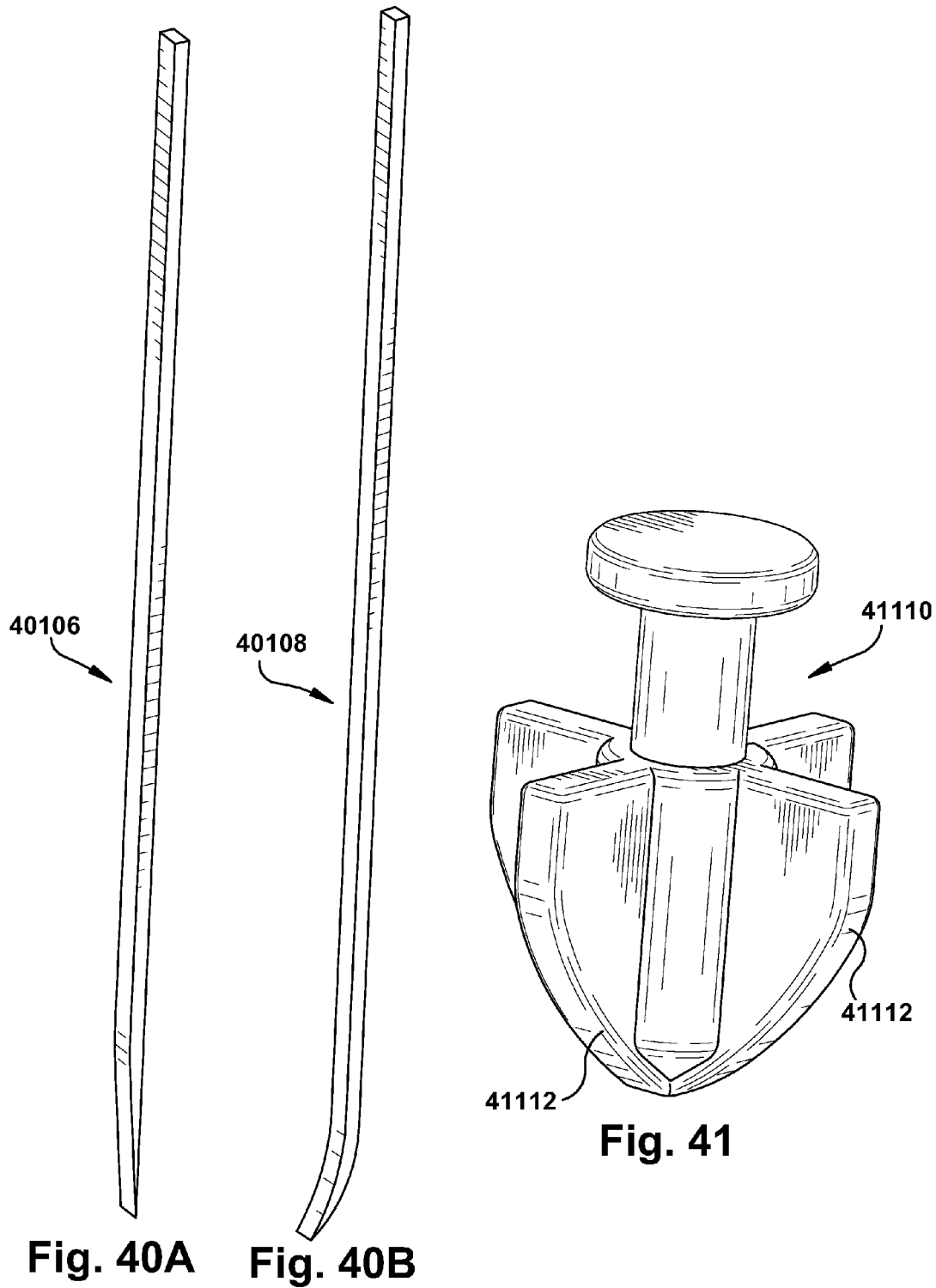
FIG. 40A is a side view of a tool for use with an embodiment of the present invention.
FIG. 40B is a side view of an alternate configuration of the tool of FIG. 40A.
FIG. 41 is a side view of a tool for use with an embodiment of the present invention.

FIG. 41 depicts a trial prosthetic implant impactor 41110. The impactor 41110 has a plurality of impactor fins 41112 which each correspond to an area of the cavity 312 where the bone was removed by a fin cutter 37100 and/or a cutter blade 39104. The surgeon can place the impactor 41110 into the cavity 312 and exert a steady and/or percussive force on the flat upper stem of the impactor to drive the impactor fins 41112 further into the cavity 312 and thereby even further clean up and define the edges of the cavity 318.

After use of the impactor 41110 and the example other tools shown in FIGS. 33A-41, or any other suitable tools, the cavity 312 will achieve a cruciform cross-sectional shape which is a concave or "negative" version of the convex or "positive" shape created by the impactor fins 41112 such that the impactor 41110 will mate into the cavity 312 reasonably closely. Alternately, the cavity 312 may be natively present and/or may be machined/formed in any suitable manner, whether or not the final shape of the cavity is configured to mate with a tool, a trial or final prosthetic implant component 1454 or any other structure.

Figure 42A:
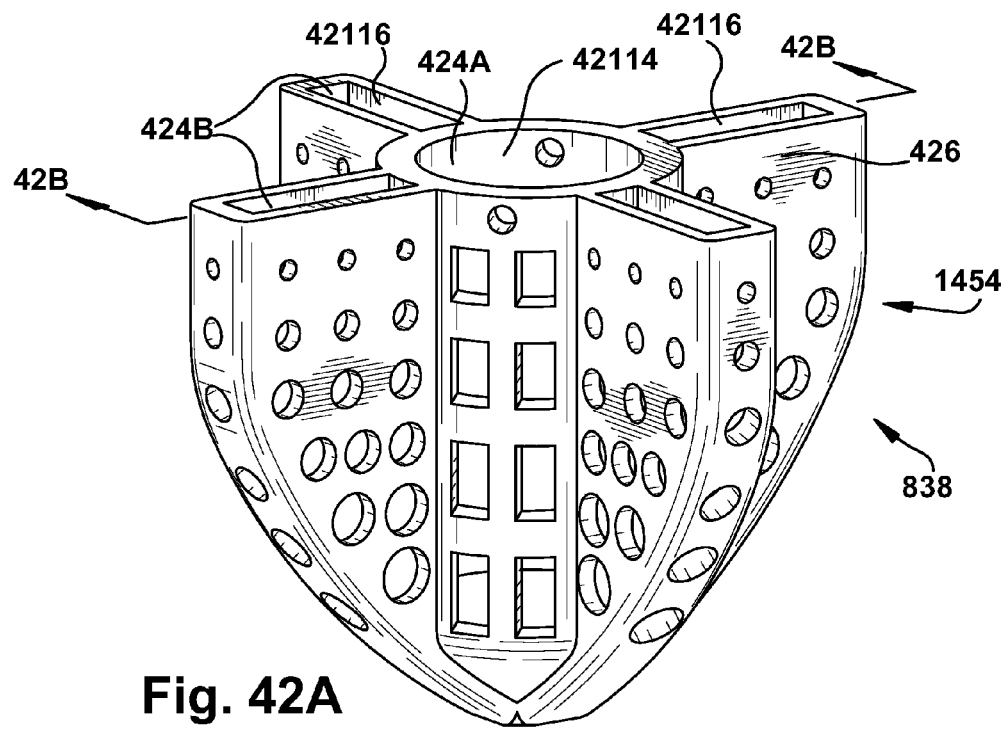
FIG. 42A is a side perspective view of an embodiment of the present invention.
Figure 42B:
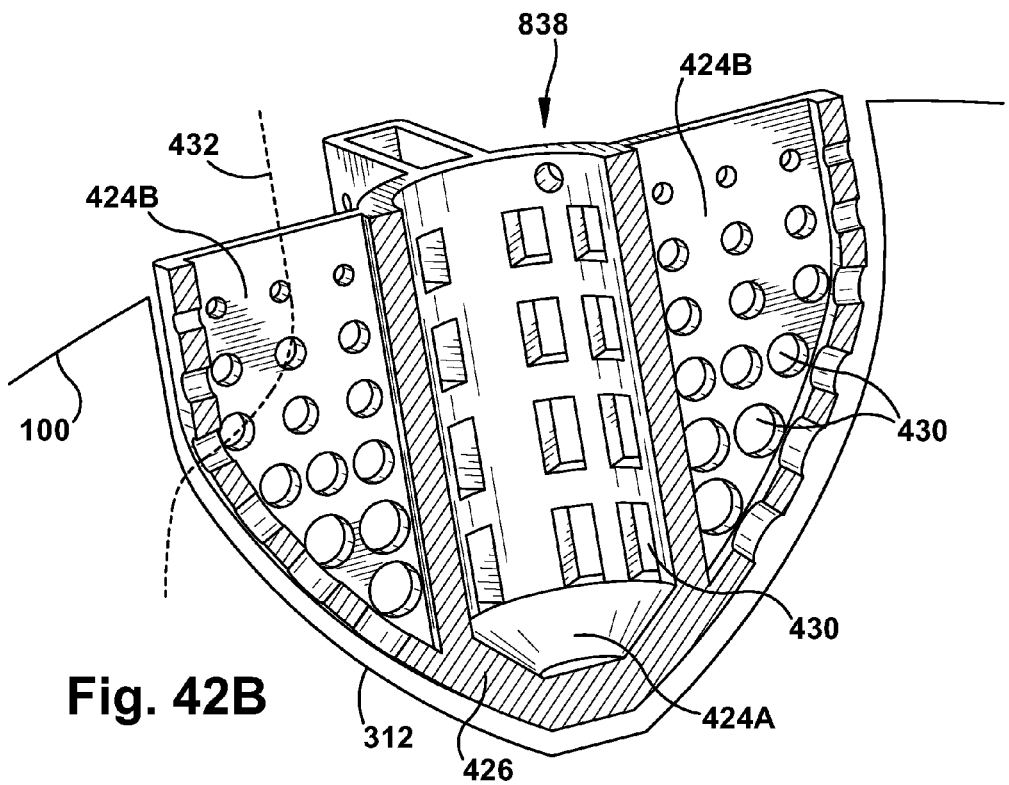
FIG. 42B is a cross-sectional view taken along line B-B of FIG. 42A.

Turning to FIGS. 42A-42B, a prosthetic implant component 1454 is shown. While the depicted prosthetic implant component 1454 is a final component, configured to remain engaged with the patient tissue at least semi-permanently, a trial component could be provided and used in a similar manner to that described and depicted herein. The prosthetic implant component 1454 of FIGS. 42A-42B has a central bore 42114 defining an interior cavity 424A which is not in fluid communication with the interior cavities 424B of the fins 42116. (A majority of the prosthetic implant component 1454 structure forms the insertion structure 838.)

The cross-sectional view of FIG. 42B shows the structure of the prosthetic implant component 1454 and the portions of the prosthetic implant component which function as structures of the bone preparation apparatus 414. An example fluid path 432 is shown extending into an interior cavity 424B of a fin 42116 of the prosthetic implant component 1454 and out through a chosen shell perforation 430 for provision and direction of fluid outside the insertion structure 838 to the patient tissue and/or the space within the cavity 312. As can be seen in FIG. 42B, the structure shell 426 is relatively thin-walled, such that a higher percentage of the total volume of the prosthetic implant component 1454 may be dedicated to interior cavity 424 space than is provided/filled by the structure shell. The interior cavity 424A of the central bore 42114 is configured for fluid communication with a manifold 416, as will be discussed below.

Figure 43A:
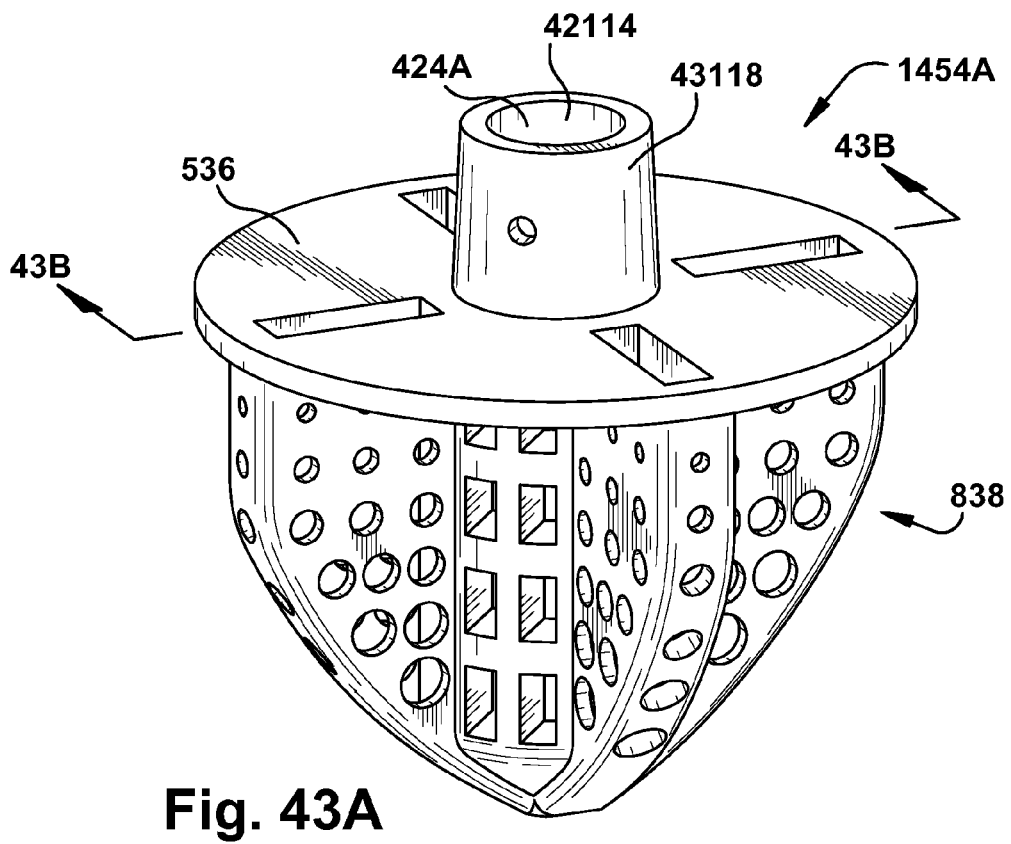
FIG. 43A is a side perspective view of an alternate configuration of the embodiment of FIG. 42A.
Figure 43B:
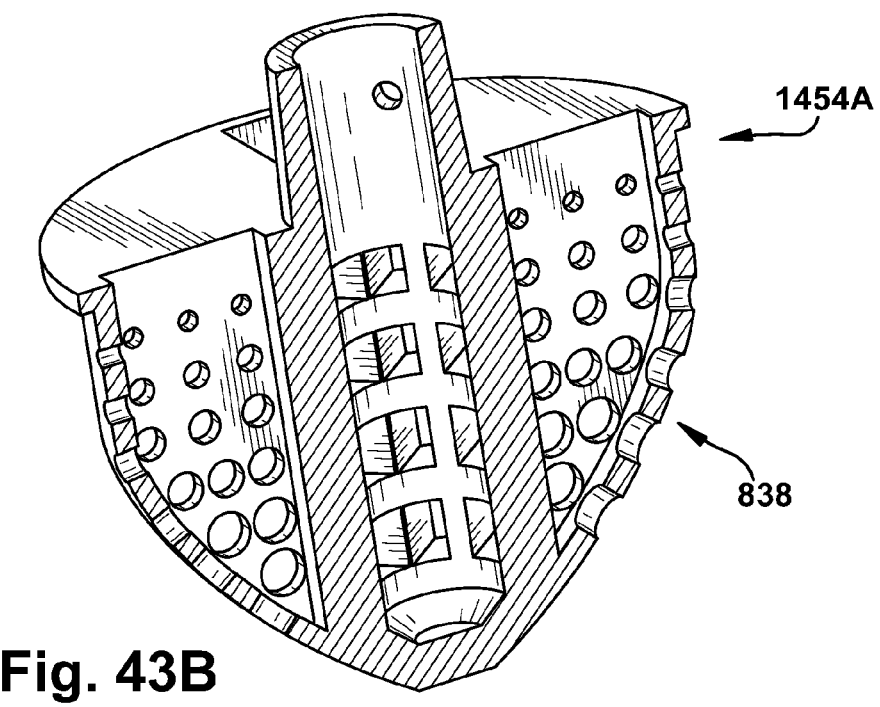
FIG. 43B is a cross-sectional view taken along line B-B of FIG. 43A.

FIGS. 43A-43B depict an alternate embodiment of the prosthetic implant component 1454A which is substantially similar to the prosthetic implant component 1454 of FIGS. 42A-42B. However, in FIGS. 43A-43B, the prosthetic implant component 1454A includes a cover plate 536 and a plate protrusion 43118, the latter in fluid communication with the interior cavity 424A of the central bore 42114. The cover plate 536 and/or plate protrusion 43118 shown in FIGS. 43A-43B may help to engage a manifold 416 in fluid communication with the interior cavities 424 in a slightly different way than that of the prosthetic implant component 1454 of FIGS. 42A-42B.

Figure 44A:
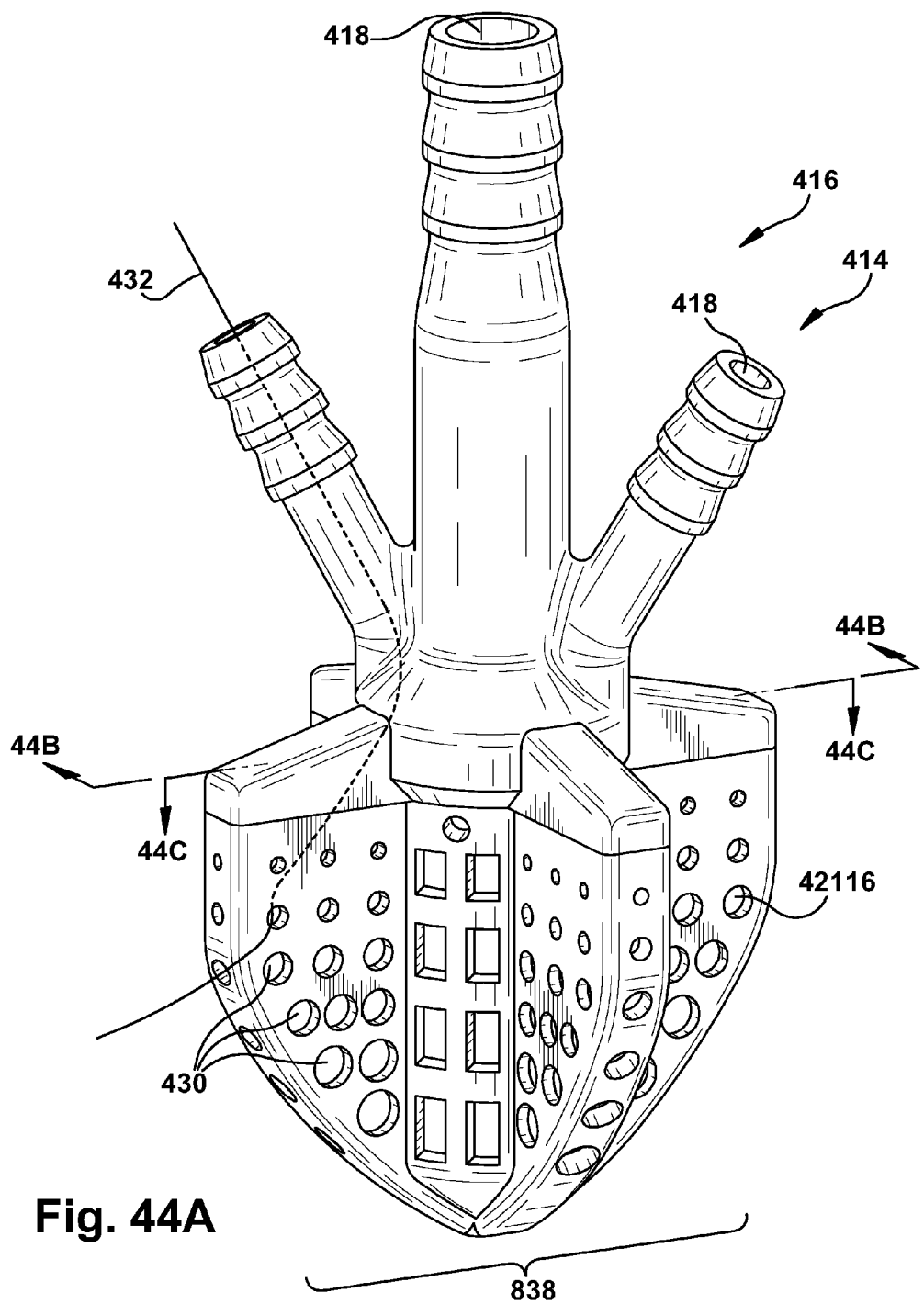
FIG. 44A is a side perspective view of the embodiment of FIG. 42A.

FIG. 44A depicts a bone preparation apparatus 414 having a prosthetic implant component 1454 (such as that depicted in FIGS. 42A-42B) serving as an insertion structure 838 and having a manifold 416 attached thereto. As shown by the example fluid path 432, any of the manifold apertures 418 can be placed into fluid communication with any of the interior cavities 424 and any of the shell perforations 430; one of ordinary skill in the art can readily provide a manifold 416 and corresponding insertion structure 838 having desired fluid path 432 properties for a particular application of the present invention.

FIG. 44B is a cross-sectional view of the bone preparation apparatus 414 shown in FIG. 44A, with additional detail showing the interior structures of the manifold 416. Here, one fluid path 432A extends through a first manifold aperture 418A for provision of a first fluid to the interior cavity 424A of the central bore 42114. A second fluid path 432B extends through a second manifold aperture 418B for provision of a second fluid (which may differ from the first fluid) to the interior cavity 424B of at least one fin 42116. The fluids may flow in the same direction or opposite directions along the first and second fluid paths 432A and 432B. The fluid(s) may be provided by one or more fluid sources 434, connected in any suitable manner to the manifold 416.

Figure 44D:
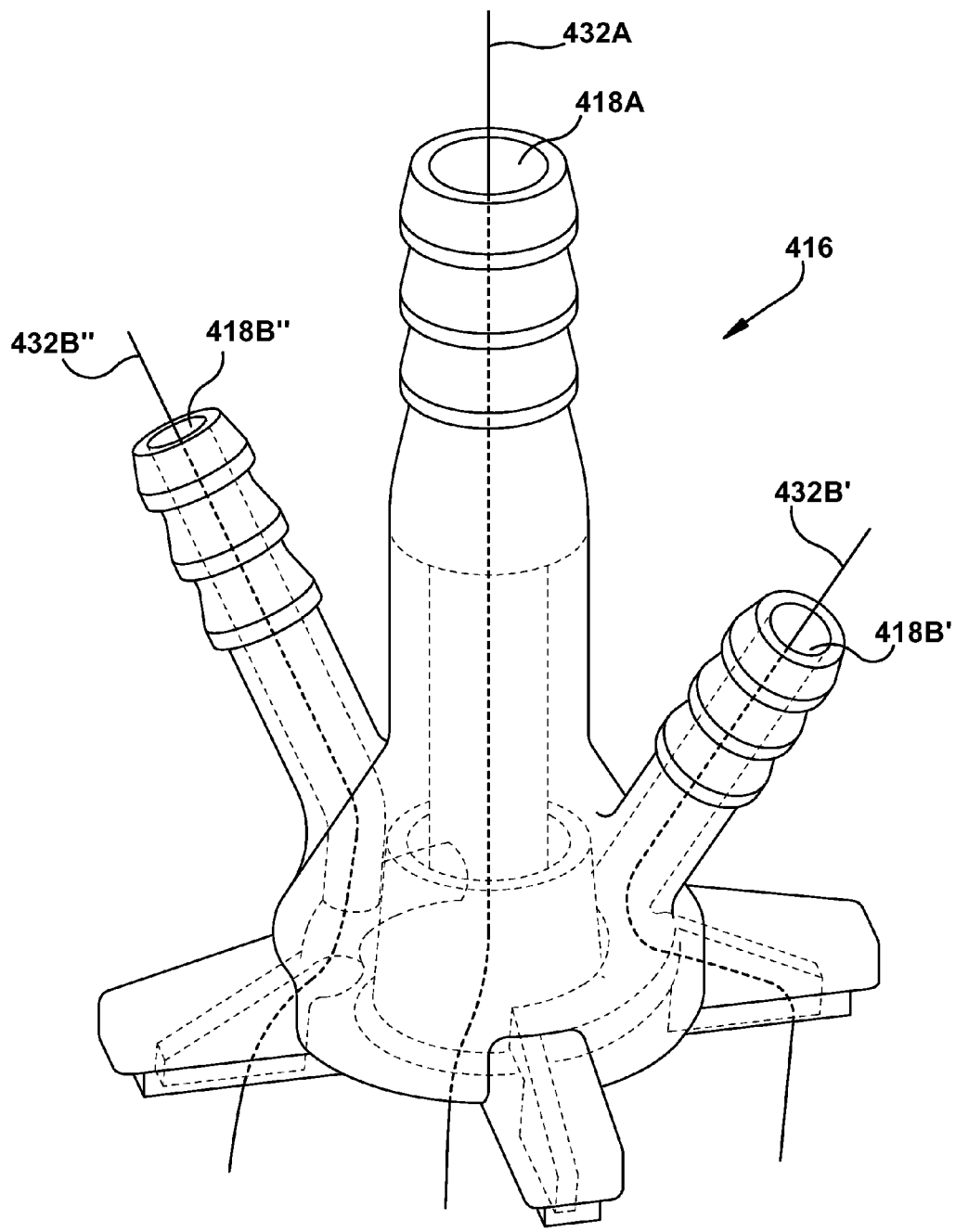
FIG. 44D is a side perspective view of the embodiment of FIG. 43A.

FIG. 44C is a cross-sectional view of a portion of the manifold 416 that shows the locations of the different manifold apertures 418A and 418B within the body of the manifold. Similarly, FIG. 44D is a partially transparent view of a manifold 416 that shows fluid paths 432A, 432B, and 432B' corresponding to manifold apertures 418A, 418B, and 418B', respectively. Using a manifold 416 similar to that shown in FIG. 44D, three different fluids can be provided to the insertion structure of FIGS. 42A-42B, as desired by the surgeon.

Figure 45:
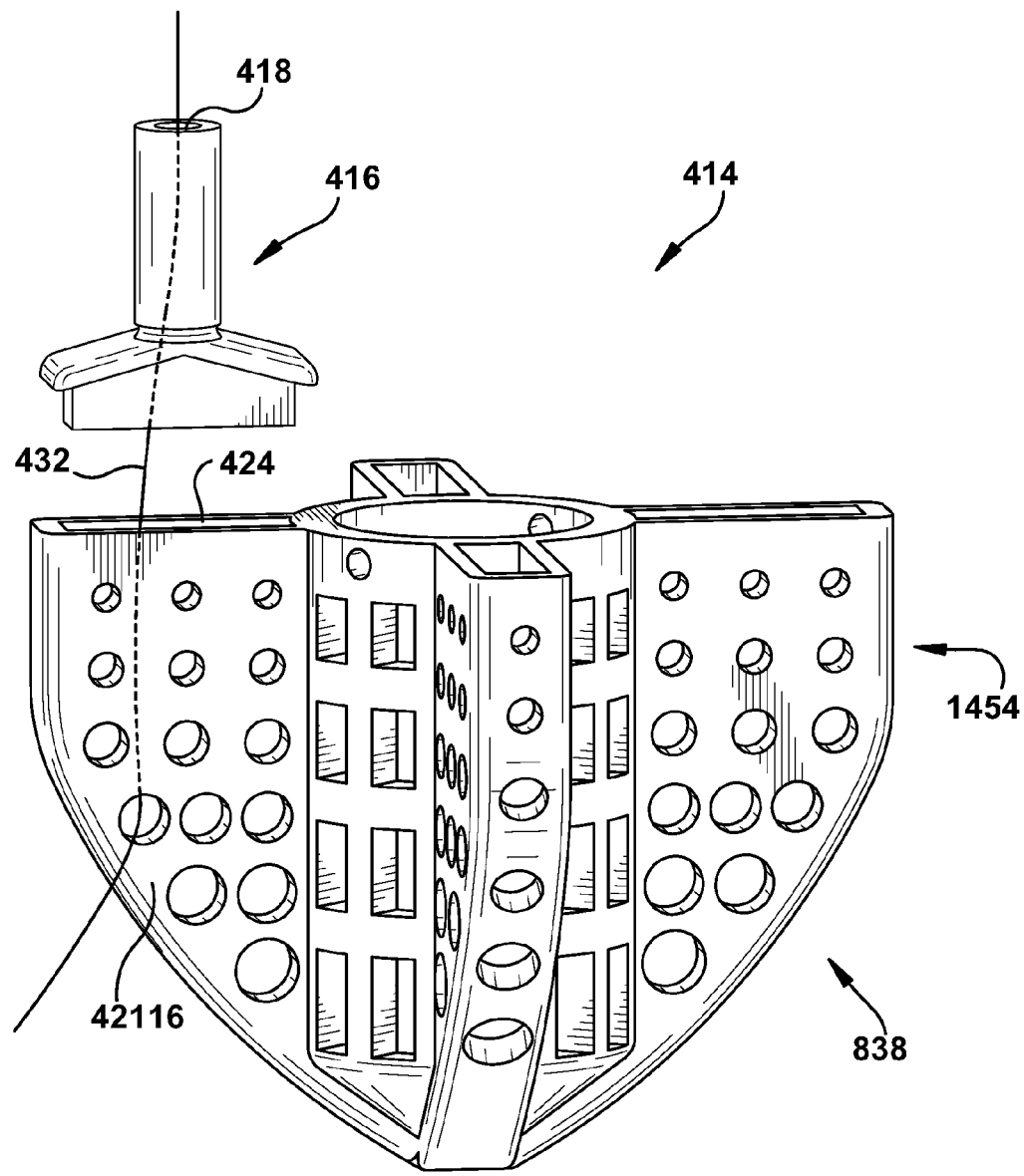
FIG. 45 is a side view of the embodiment of FIG. 42A.

FIG. 45 shows an exploded view of an alternate means of providing fluid to one or more fins 42116. In FIG. 45, a relatively simple and compact manifold 416 (when compared to the manifold of FIGS. 44A-44C), configured to mate with an interior cavity 424 of a chosen one of the fins 42116, may be placed individually into contact with any or all of the fins of a particular insertion structure 838 (here, the fins are part of a prosthetic implant component 1454). A fluid path 432 can be created and a fluid provided at least one of proximate and contacting a patient tissue beneath an outer surface thereof.

The bone preparation apparatus 414 may be configured to the shape and/or dimensions of the cavity 312, or vice versa. The bone preparation apparatus 414 may be a template, configurable to the size of the implant, and/or may itself be implantable. The bone preparation apparatus 414 may be cannulated and/or include one or more shell perforations 430 along its surface to allow for suction, irrigation, and/or injection of fixation and/or bone enhancement materials, or any other suitable materials. The bone preparation apparatus 414 (whether or not it also includes structures functioning as a prosthetic implant component 1454) may allow for preparation of the bone marrow space adjacent to the bone preparation apparatus, removal of the marrow elements, and/or creation of a cavity 312 in the patient tissue adjacent to and/or approximately sized to the insertion structures 838 of the bone preparation apparatus 414.

Embodiments may include the injection of fixation material, for example, in a liquid or semi-liquid state. The fixation material(s) may be injected into a bone preparation apparatus 414 serving as a trial or template of a final prosthetic implant component 1454. The added fixation materials may be dispersed using a fluid source 434, for example, that used with the bone preparation apparatus 414. The bone preparation apparatus 414 may include part of the final prosthetic implant component 1454. The fixation materials may be placed adjacent to the prosthetic implant component 1454 to reinforce the bone, preferably in the area to be used for implant fixation. Embodiments may allow fixation materials to be placed in areas not easily accessible using traditional methods. Embodiments may allow for preservation of the bone structure, marrow, and/or other tissue elements. Bone or other patient tissue spaced apart from the bone preparation apparatus 414 may be kept intact and/or may be prepared and augmented with standard bone preparation methods.

The bone preparation apparatus 414 may be made of any material mentioned in the present disclosure or known in the art. The bone preparation apparatus 414 may be made of a reusable or disposable material. Embodiments may first perform suction and/or irrigation to prepare the bone, and then add the bone filler or PMMA cement to the prepared bone. Embodiments may be impacted using a tamp or series of tamps that have and maintain the shape of the bone preparation apparatus 414 and/or the prosthetic implant component 1454.

Embodiments of the present disclosure may relate to bone preparation instruments and/or implants. A device may be attached to an instrument or implant to provide suction, irrigation or injection of material through the instrument or device into the surrounding cancellous bone. Embodiments may increase or decrease fixation, for example, by including perforations, slots, bumps, textures, or other features for facilitating fixation with bone. Such features may allow for preparation of the bone, addition of materials, and/or stabilization of an implant. Embodiments may be configured for use with instruments, trials, temporary implants, permanent implants, broaches, and any other device suitable for use within a body. For example, embodiments may be used for orthopedic surgery, hip, knee and shoulder replacements, maxillofacial surgery, dental implants, internal fixation devices for fractures or fracture sequelae, suture anchors for soft tissue to bone repair, and external fixation devices. The implant or instrument provides a mechanism for modification of the bone through the instrument or implant. Additionally, embodiments may be configured to adjust and/or enhance the fixation of the implant, for example, to bone, soft tissue, and/or another implant.

Embodiments may be positioned a distance from a prepared bone surface and/or utilized for setting weakened and/or cancellous bone. Example embodiments may be dimensioned and configured for preparing bone, providing irrigation, providing suction, providing growth promoting materials, and/or providing materials for hemostasis. Embodiments may be configured to remove materials (e.g., marrow, tissue, unwanted materials, any material mentioned in the present disclosure or known in the art, or any combination thereof) and/or to add materials (e.g., synthetic materials, biologic materials, matrix, cells or growth factors, fixation materials, therapeutic substances, any other material mentioned in the present disclosure or known in the art, or any combination thereof).

Additionally, embodiments may be positioned with respect to an implant, for example in an area adjacent to the implant. Embodiments may be configured to allow for placement of bone cement, bone graft materials, bone graft substitute material, synthetic materials, biologic materials, non-biologic materials, and/or any material mentioned in the present disclosure or known in the art or any combination thereof. Embodiments may improve the immediate-, short-, and/or long-term fixation of the implant, for example, by enhancing the structure of the bone adjacent to the implant.

Additional embodiments may be configured to place materials at the prosthetic-bone interface. Materials may be placed over the entire surface or confined to selected areas. Materials may be applied while the device is in situ to enhance the fixation and/or allow for the uniform and/or direct addition of materials at the prosthetic-bone interface.

Embodiments may be any material suitable for use in the body, for example, porous, natural, and/or absorbable materials. Embodiments may be patient-specific to the patient's dimensions and/or the surgical site. Embodiments may include metals, polymers, or any other biocompatible material. Embodiments may include smooth, roughened, and/or porous surfaces. Embodiments may be formed with cavities or other shapes. Embodiments may include stainless steel, shape memory alloys (e.g., Nitinol), tantalum, porous tantalum, titanium, cobalt-chrome alloys, and/or any other material mentioned in the present disclosure or known in the art or any combination thereof.

Embodiments may include a screw, intermedullary rod, plate, external fixation pin, stem, suture anchor, and/or fixation devices or mechanisms to secure an implant to patient tissue and/or to another implant—for example, securing a prosthetic to bone. An embodiment may include a central void, potentially with perforations along a portion of or its entire surface. The perforations, when present may be configured for the suction, injection, and/or irrigation of the bone material adjacent to the implant and/or injection of a filler material (e.g., bone graft material, bone graft substitutes, hemostatic agents [pharmacologic or physical materials], growth factors, biologic materials, cells with or without a matrix scaffold, and/or any material mentioned in the present disclosure or known in the art or any combination thereof).

Additional embodiments may include application in the spine, extremities, axial skeleton, craniofacial, or any other suitable bones. Embodiments may be applied in fracture reconstruction, primary or revision joint replacement, traumatic and arthritic conditions, tumor reconstruction, soft tissue to bone repair, in conjunction with suture anchors, and/or for management of pediatric bone lesions. Embodiments may be used for bone preparation, bone augmentation, and/or implants. Embodiments may improve immediate and/or long-term fixation of an implant.

Embodiments may at least partially include, and/or be positioned, attached, and/or stabilized relative to each other or relative to a portion of a body of a patient and/or another implant using, any one or more of the following materials and/or configurations, or any other suitable material and/or physical treatment or property: polymethylmethacrylate ("PMMA"); bone cement; glue; adhesive (e.g., bone adhesive); grouting agents; bone graft substitute; injectable materials; synthetic materials; natural materials; acrylics; materials that are bondable, biocompatible, degradable, biodegradable, bioerodible, bioabsorbable, mechanically expandable, hydrophilic, bendable, deformable, and/or malleable; and connections and/or components that are riveted, threaded, toggling, barbed, bubbled, laminated, coated, blocking, pneumatic, one-piece, multi-component, solid, hollow, polygon-shaped, pointed, and/or self-introducing. Also, embodiments may include, but are not limited to, being comprised partially or entirely of a metallic material, polymeric material, ceramic material, composite material, body tissue from any source, synthetic tissue, hydrophilic material, expandable material, compressible material, bondable material, and/or any material disclosed in the present disclosure or known in the art or any combination thereof.

Further embodiments may be configured to include other parts of any suitable fixation mechanism—for example, by connecting component parts to standard and/or traditional parts of a final or trial implant. Embodiments may be connectable through a taper (e.g., Morse taper), screw, thread, locking mechanism, slip fit, interference fit, press fit, adhesive, bondable material, and/or any material mentioned in the present disclosure or known in the art or any combination thereof.

Fixation of a prosthetic implant component 1454 may be enhanced using the disclosed bone preparation apparatus 414 with the aid of a fixation material (e.g., a bone filler, bone graft substitute, and/or bone cement). The fixation material may be placed relative to the bone, then, the fixation material may be impacted. Preferably, the fixation material should reach the marrow space of a bone for some use environments of the present invention. Pulsatile irrigation may be used, with or without a bone preparation apparatus 414, to remove a portion or all of the marrow elements before placement of the fixation material, which may facilitate penetration of the fixation material into the bone surface. After at least a portion of the fixation material has been added, the implant may be placed into position. Irrigation and/or the addition of fixation material may be achieved with a typical or stock instrument, which need not be specific to the implant size, shape or location of the implant, or may be accomplished with the help of the disclosed bone preparation apparatus 414.

Bone preparation may also be performed with non-biologic material, such as glue, PMMA, or a bioabsorbable bone graft substitute or biologic material consisting or cells, matrix carrier, bioactive molecules, and/or any material mentioned in the present disclosure or known in the art or some combination thereof.

Embodiments may include therapeutic substances—for example, antibiotics, hydroxyapatite, anti-inflammatory agents, steroids, antibiotics, analgesic agents, chemotherapeutic agents, bone morphogenic protein ("BMP"), demineralized bone matrix, collagen, growth factors, autogenic bone marrow, progenitor cells, calcium sulfate, immunosuppressants, fibrin, osteoinductive materials, apatite compositions, germicides, fetal cells, stem cells, enzymes, proteins, hormones, cell therapy substances, gene therapy substances, and/or any material mentioned in the present disclosure or known in the art or any combination thereof. These therapeutic substances may be combined with the materials used to make the device or may be separately provided.

Embodiments may include one or more tubes, pylons, ducts, channels, conduits, cannulations, or the like (referred to throughout as "tubes"), which may include one or more perforations, fenestrations, apertures, punctures, or the like (referred to throughout as "perforations"). Embodiments may include tools and/or instruments, which may include reusable, absorbable, and/or synthetic materials that may remain in situ or be removed. For example, an injection tool may be inserted, potentially relative to or into pre-drilled holes.

Embodiments may include a pressure instrument, for example, any suction, irrigation, injection, pump, infusion, pneumatic, or compression device, or any device capable of creating positive or negative pressure. The pressure instrument may be attachable to any or all the tubes. The pressure instrument may include a cannulated manifold for suction and/or irrigation of bone and/or the addition of materials to the surrounding tissue and/or bone matrix. In this embodiment, the implant and/or tool may remain in position if made of a resorbable material, or, if removed, holes may be filled with the same and/or new bone enhancement material. If this method is applied shortly before insertion of a durable prosthetic implant, the material injected into the bone may be, for example, a resorbable bone graft substitute, which could provide additional structural support for the bone when hardened. After bone preparation, with or without leaving the injection tool in place, the bone could be further prepared using standard instrumentation.

In any embodiment of the present invention, the manifold 416 may be of relatively rigid construction, or may instead be at least partially made of a flexible material, to facilitate bending of the manifold to place the manifold apertures 418 into desired relationships with the interior cavities 424 of the insertion structure 838.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the bone preparation apparatus 414 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. A fluid could fill one or more interior cavities 424 and remain therein during semi-permanent maintenance of the prosthetic implant component 1454 within the patient tissue—for example, the interior cavities of the prosthetic implant component could be filled with bone cement, which is then permitted to harden and thereby strengthen the prosthetic implant component into a relatively solid "block" of material. The bone preparation apparatus 414 may include a plurality of structures cooperatively forming any components thereof and temporarily or permanently attached together in such a manner as to permit relative motion (e.g., pivoting, sliding, or any other motion) therebetween as desired. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A method for patient tissue preparation, comprising the steps of:

providing a manifold having at least one manifold aperture extending therethrough;

placing the manifold aperture in fluid communication with a fluid source;

providing an insertion structure having a plurality of interior cavities, each interior cavity being at least partially defined by a structure shell, with at least one interior cavity having at least one of a length, width, and cross-sectional shape which is different from at least one of a length, width, and cross-sectional shape of another one of the interior cavities;

placing at least a chosen interior cavity in fluid communication with a corresponding manifold aperture;

selectively placing the insertion structure in a penetrating relationship with a patient tissue below a surface of the patient tissue;

providing at least one shell perforation extending through the structure shell;

placing the chosen interior cavity in fluid communication with a surrounding ambient space through at least one shell perforation;

when the insertion structure is in the penetrating relationship with the patient tissue, creating at least one fluid path extending from the fluid source, through the manifold aperture, into the chosen interior cavity, through at least one shell perforation, and at least one of a proximate relationship and a contacting relationship with the patient tissue beneath the outer surface thereof; and directing a fluid along the fluid path to perform a patient tissue preparation task.

2. The method of claim 1, wherein the step of providing an insertion structure includes the step of providing a tube having proximal and distal tube ends separated by a tube body defining at least a portion of the chosen interior cavity;
   wherein the step of providing at least one shell perforation extending through the structure shell includes the step of providing at least one tube perforation therethrough;
   wherein the step of placing the chosen interior cavity in fluid communication with a corresponding manifold aperture includes the step of selectively placing the proximal tube end in fluid communication with the fluid source through connection with a chosen manifold aperture;
   wherein the step of selectively placing the insertion structure in a penetrating relationship with a patient tissue below a surface of the patient tissue includes the step of placing the distal tube end in penetrating insertion into the patient tissue with at least one tube perforation located beneath an outer surface of the patient tissue; and
   wherein the step of creating at least one fluid path includes creating a fluid path extending through the manifold aperture, into the proximal tube end, through the tube body, through the tube perforation, and at least one of proximate and contacting the patient tissue beneath the outer surface thereof.

3. The method of claim 1, including the steps of:
   at least semi-permanently placing the insertion structure into the penetrating relationship below the patient tissue surface during a surgical procedure; and
   allowing the insertion structure to remain in the penetrating relationship after the surgical procedure ends.

4. The method of claim 1, wherein the step of providing at least one shell perforation includes the step of providing a plurality of shell perforations, with at least one shell perforation having a chosen one of a length, width, perimeter shape, and angle of penetration through the structure shell which is different from a corresponding chosen one of a length, width, perimeter shape, and angle of penetration through the structure shell of another one of the shell perforations.

5. The method of claim 1, including the step of altering the patient tissue to accept in a mating relationship an insertion structure having a particular physical configuration property before the insertion structure is placed into the penetrating and mating relationship with the patient tissue.

6. The method of claim 1, including the step of substantially separating at least one fluid path laterally from at least one other fluid path by intervening patient tissue when the insertion structure is in the penetrating relationship with the patient tissue.

7. A method for patient tissue preparation, comprising the steps of:
   providing a manifold having at least one manifold aperture extending therethrough;
   placing the manifold aperture in fluid communication with a fluid source;
   providing a plurality of insertion structures, each insertion structure having at least one interior cavity at least partially defined by a structure shell;
   placing each interior cavity in fluid communication with a corresponding manifold aperture;
   temporarily and substantially simultaneously placing each insertion structure in a penetrating relationship with a patient tissue below a surface of the patient tissue during a surgical procedure;
   removing each insertion structure from the penetrating relationship before the surgical procedure ends;
   providing at least one shell perforation extending through the structure shell;
   placing the interior cavity in fluid communication with a surrounding ambient space through at least one shell perforation;
   when each insertion structure is in the penetrating relationship with the patient tissue, creating at least one fluid path extending from the fluid source, through the manifold aperture, into the interior cavity, through at least one shell perforation, and at least one of a proximate relationship and a contacting relationship with the patient tissue beneath the outer surface thereof; and
   directing a fluid along the fluid path to perform a patient tissue preparation task.

8. A method for patient tissue preparation, comprising the steps of:
   providing a manifold having at least one manifold aperture extending therethrough;
   placing the manifold aperture in fluid communication with a fluid source;
   providing an insertion structure having at least one interior cavity at least partially defined by a structure shell;
   placing the interior cavity in fluid communication with a corresponding manifold aperture;
   selectively placing the insertion structure in a penetrating relationship with a patient tissue below a surface of the patient tissue;
   providing at least one shell perforation extending through the structure shell;
   placing the interior cavity in fluid communication with a surrounding ambient space through at least one shell perforation;
   when the insertion structure is in the penetrating relationship with the patient tissue, creating at least one fluid path extending from the fluid source, through the manifold aperture, into the interior cavity, through at least one shell perforation, and at least one of a proximate relationship and a contacting relationship with the patient tissue beneath the outer surface thereof; and
   directing a fluid along a first fluid path in a first direction from the fluid source, through the manifold aperture, into the interior cavity, and through the at least one shell perforation to perform a patient tissue preparation task; and
   directing a fluid along a second fluid path in a second direction, opposite the first direction, through the at least one shell perforation, into the interior cavity, through the manifold aperture, and to the fluid source to perform a patient tissue preparation task.

* * * * *

UNITED STATES PATENT AND TRADEMARK OFFICE
CERTIFICATE OF CORRECTION

| | | |
|---|---|---|
| PATENT NO. | : 9,216,046 B2 | Page 1 of 1 |
| APPLICATION NO. | : 13/443555 | |
| DATED | : December 22, 2015 | |
| INVENTOR(S) | : Joseph P. Iannotti et al. | |

It is certified that error appears in the above-identified patent and that said Letters Patent is hereby corrected as shown below:

In the claims,

Claim 1, column 24, line 46 reads "with at least one interior cavity having at least one of a length, width, and cross-sectional shape which is different from at least one of a length, width, and cross-sectional shape of another one of the interior cavities;" should read --with at least one interior cavity having a different physical configuration property from another one of the interior cavities;--

Signed and Sealed this
Third Day of May, 2016

Michelle K. Lee
*Director of the United States Patent and Trademark Office*